(12) United States Patent
Lieberman

(10) Patent No.: US 6,551,320 B2
(45) Date of Patent: *Apr. 22, 2003

(54) METHOD AND APPARATUS FOR CORRECTING SPINAL DEFORMITY

(75) Inventor: Isador H. Lieberman, Pepper Pike, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 09/899,669

(22) Filed: Jul. 5, 2001

(65) Prior Publication Data

US 2002/0055740 A1 May 9, 2002

Related U.S. Application Data

(63) Continuation-in-part of application No. 09/812,085, filed on Mar. 19, 2001, which is a continuation-in-part of application No. 09/781,847, filed on Feb. 14, 2001, which is a continuation-in-part of application No. 09/708,940, filed on Nov. 8, 2000, and a continuation-in-part of application No. 09/708,292, filed on Nov. 8, 2000, now Pat. No. 6,468,309.

(51) Int. Cl.$^7$ ............................................. A61B 17/56
(52) U.S. Cl. .................................... 606/61; 606/86
(58) Field of Search ........................ 606/61, 69, 70, 606/71, 72, 86

(56) References Cited

U.S. PATENT DOCUMENTS

| | | | | |
|---|---|---|---|---|
| 2,033,039 | A | | 3/1936 | Limpert ................. 24/710.9 |
| 4,041,939 | A | * | 8/1977 | Hall ............................ 606/61 |
| 4,762,453 | A | | 8/1988 | DeCaro ..................... 411/383 |

(List continued on next page.)

FOREIGN PATENT DOCUMENTS

| | | |
|---|---|---|
| EP | 0374088 A1 | 6/1990 |
| EP | 0663184 A1 | 7/1995 |
| FR | 2299548 | 8/1976 |
| SU | 1071297 A | 2/1984 |
| WO | WO224087 A1 | 3/2002 |

OTHER PUBLICATIONS

An article entitled "Anterior Vertebral Body Screw Pullout Testing, A Comparison of Zielke, Kaneda, Universal Spine System, and Universal Spine System with Pullout–Resistant Nut", by Isador H. Lieberman et al., reprinted from SPINE, vol. 23, No. 8, Apr. 15, 1998.

An excerpt from *The Application of Shape Memory Alloys in Medicine*; Author: I. P. Lipscomb, 1996; Contents; Forward; Preface; Chapter 1 "Introduction to Shape Memory Alloys (SMAs)".

An excerpt from *The Application of Shape Memory Alloys in Medicine*; Author: I. P. Lipscomb, 1996; Chapter 2 entitled "Characteristics of Shape Memory Alloys in Medical Applications".

An excerpt from *The Application of Shape Memory Alloys in Medicine*; Author: I. P. Lipscomb, 1996; Chapter 5 "Present and Future Orthopaedic Applications".

*Primary Examiner*—John J. Wilson
(74) *Attorney, Agent, or Firm*—Tarolli, Sundheim, Covell & Tummino L.L.P.

(57) ABSTRACT

An apparatus (10) for correcting spinal deformity comprises at least one anchor (20) for implantation into a vertebral body (90). The anchor (20) includes a platform (24) having a first surface (38) for facing the vertebral body (90). The anchor (20) further includes screw means (50 and 52) for embedding into the vertebral body (90) upon rotation of the platform (24). The platform (24) includes at least one passage (44) extending transversely through the platform. The passage (44) receives a cable (120) connected with another anchor (20) in another vertebral body (92). The cable (120) is tensioned to cause relative movement between the vertebral bodies (90 and 92) and thereby correct the spinal deformity. Additional cables (150, 170) may be connected to the anchors (20) and tensioned to achieve correction in multiple planes.

38 Claims, 18 Drawing Sheets

U.S. PATENT DOCUMENTS

| | | | |
|---|---|---|---|
| 4,790,303 A | * 12/1988 | Steffee | 606/61 |
| 4,854,311 A | 8/1989 | Steffee | 606/66 |
| 5,055,104 A | 10/1991 | Ray | 606/61 |
| 5,246,443 A | * 9/1993 | Mai | 606/78 |
| 5,263,953 A | 11/1993 | Bagby | 606/61 |
| 5,290,289 A | 3/1994 | Sanders et al. | 606/61 |
| 5,534,031 A | 7/1996 | Matsuzaki et al. | 623/17 |
| 5,582,616 A | 12/1996 | Bolduc et al. | 606/143 |
| 5,626,613 A | 5/1997 | Schmieding | 606/232 |
| 5,662,683 A | 9/1997 | Kay | 606/232 |
| 5,690,629 A | 11/1997 | Asher et al. | 606/61 |
| 5,728,116 A | 3/1998 | Rosenman | 606/151 |
| 5,782,831 A | 7/1998 | Sherman et al. | 606/61 |
| 5,791,899 A | 8/1998 | Sachdeva et al. | 433/173 |
| 5,810,851 A | 9/1998 | Yoon | 606/148 |
| 5,824,008 A | 10/1998 | Bolduc et al. | 606/43 |
| 5,904,696 A | 5/1999 | Rosenman | 606/151 |
| 6,036,701 A | 3/2000 | Rosenman | 606/151 |
| 6,086,590 A | 7/2000 | Margulies et al. | 606/61 |
| 6,113,638 A | * 9/2000 | Williams et al. | 606/61 |
| 6,296,656 B1 | 10/2001 | Bolduc et al. | 606/213 |

* cited by examiner

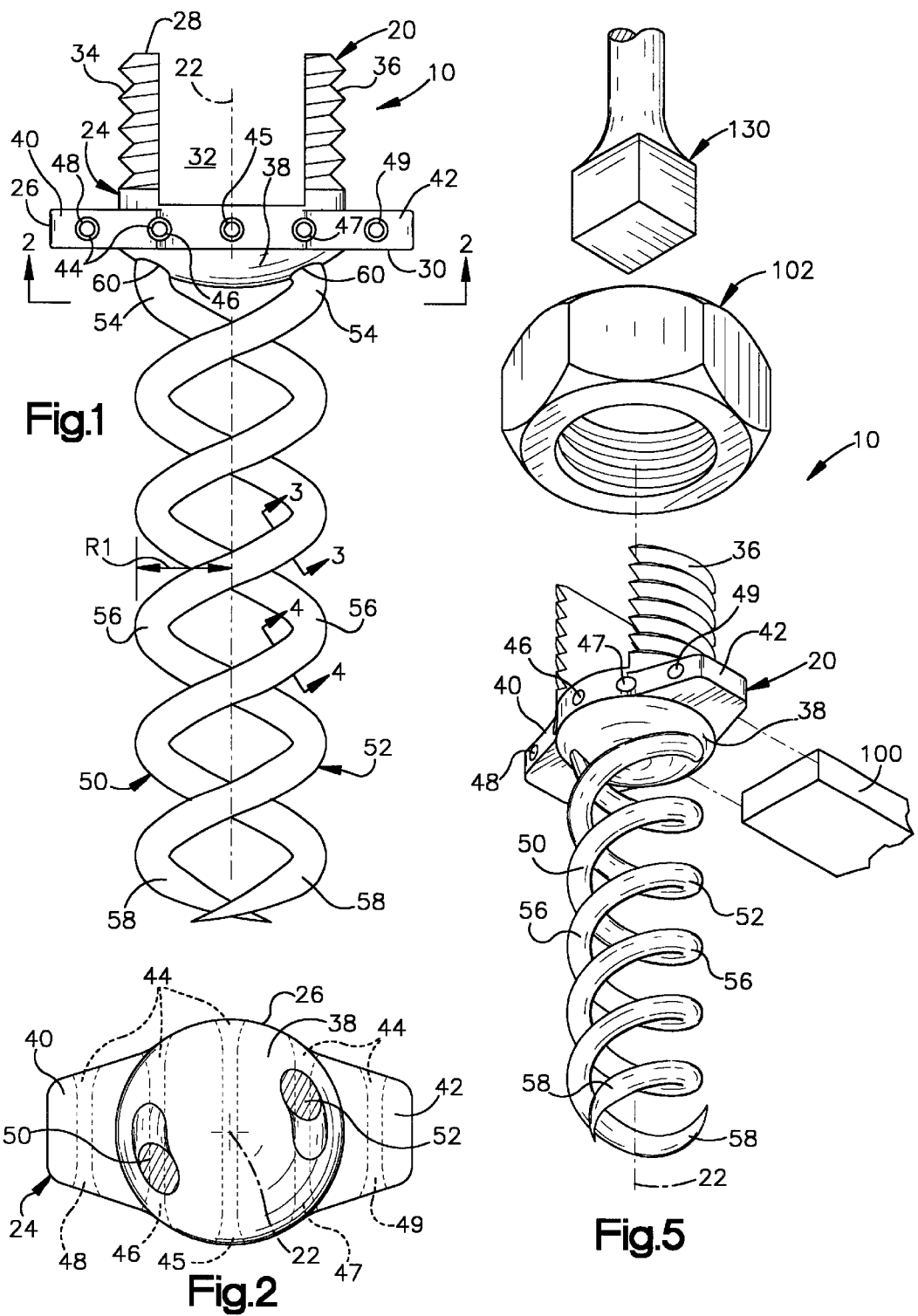

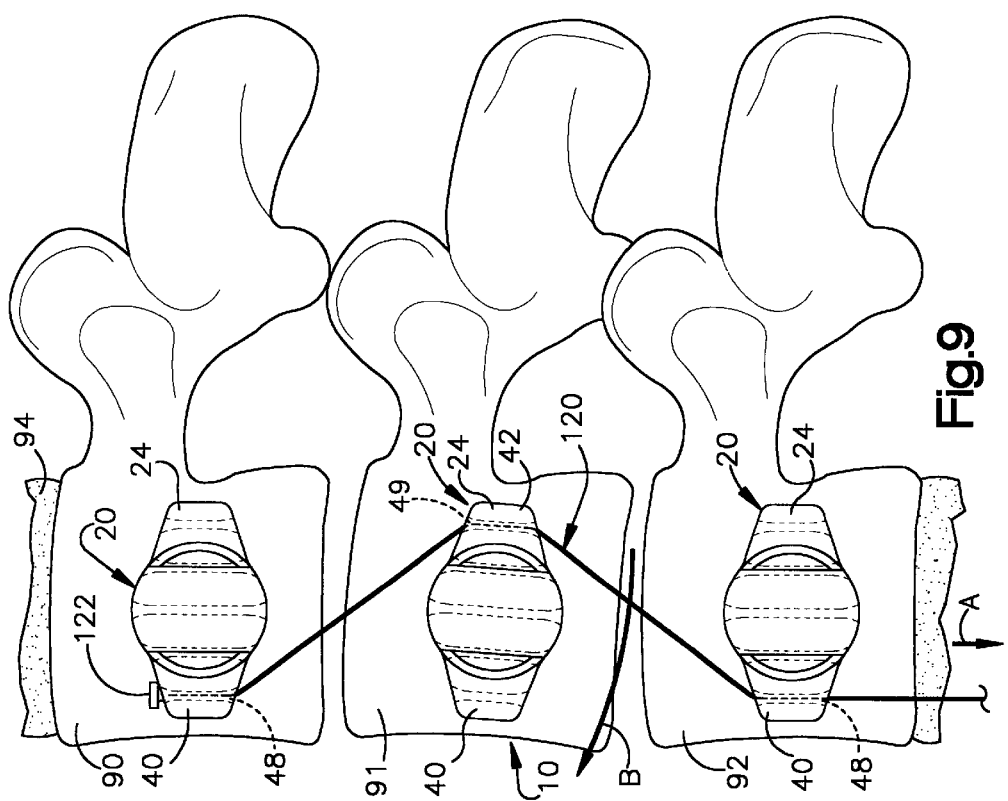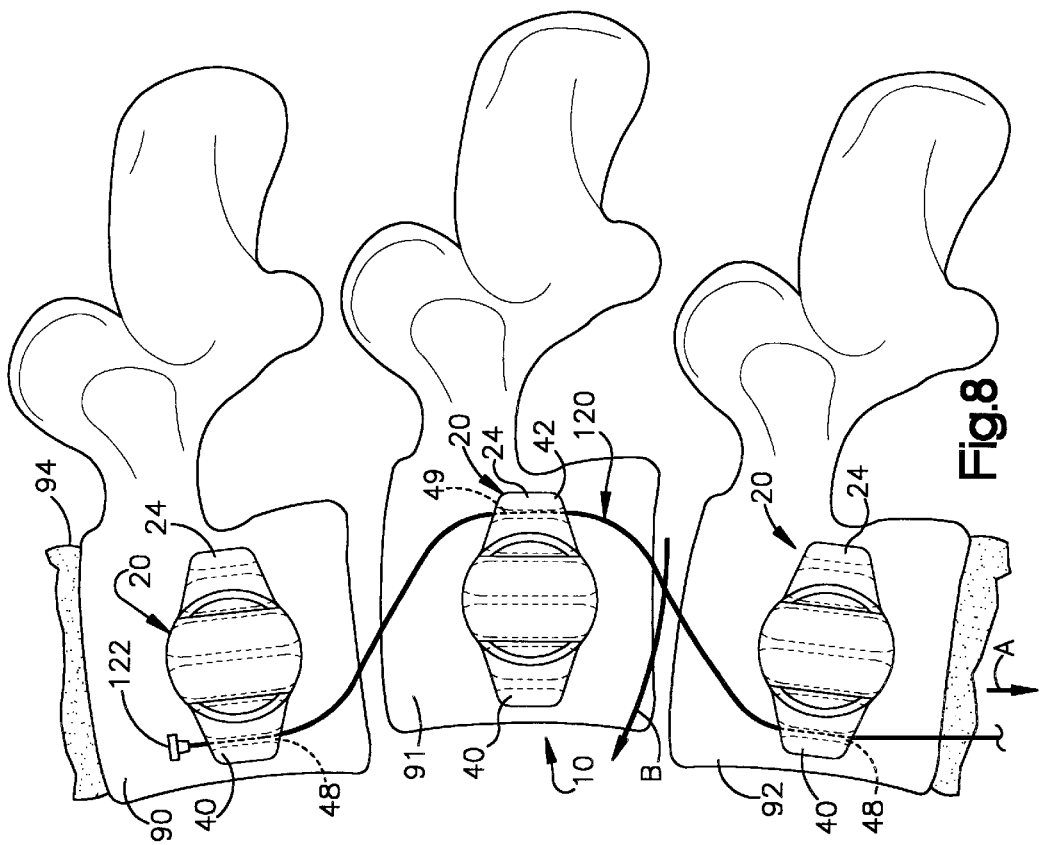

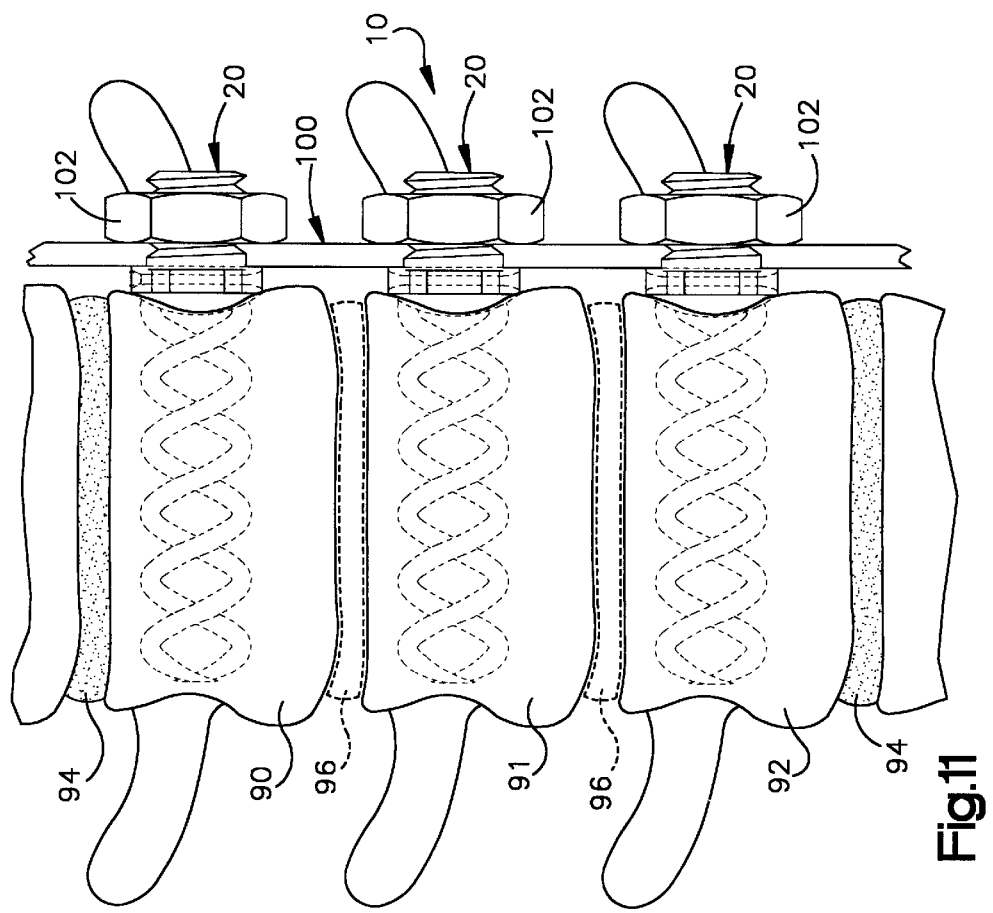
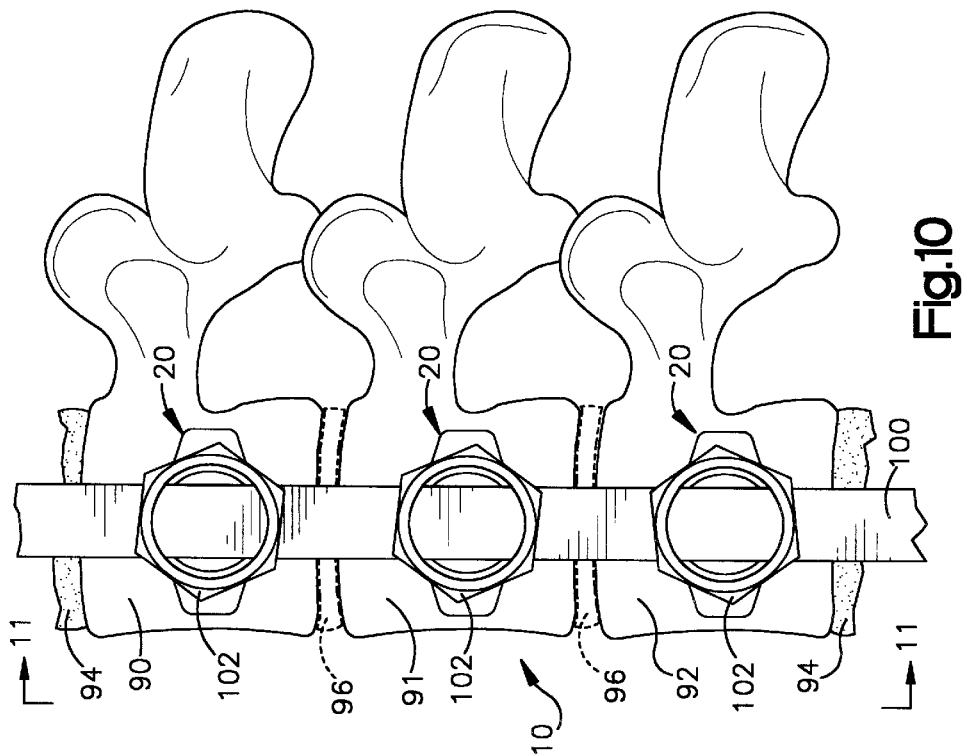

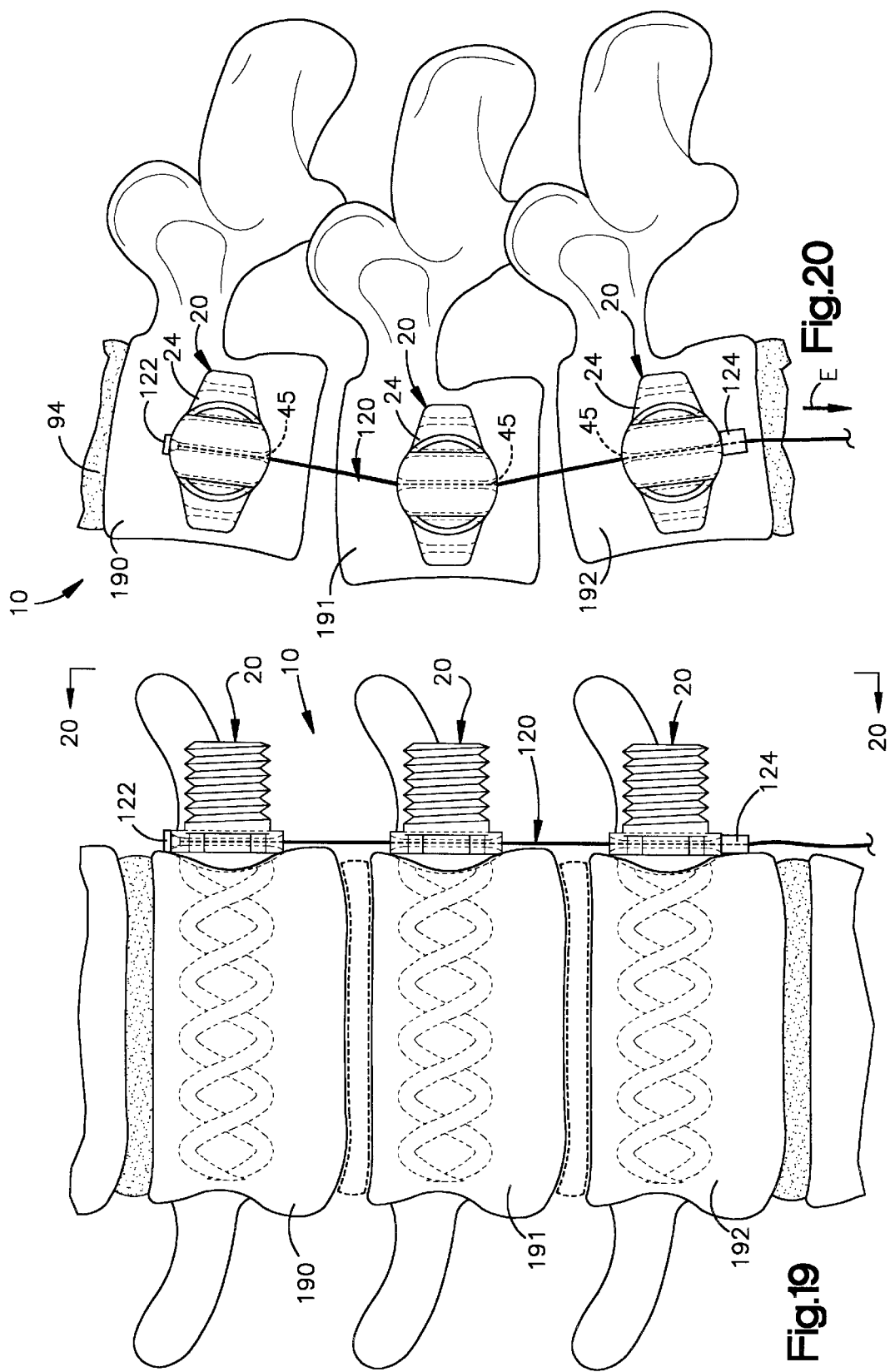

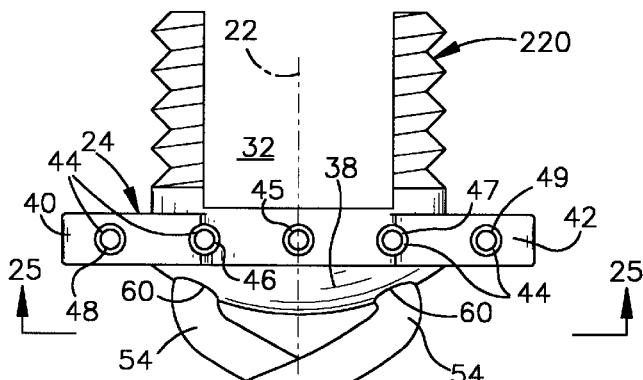
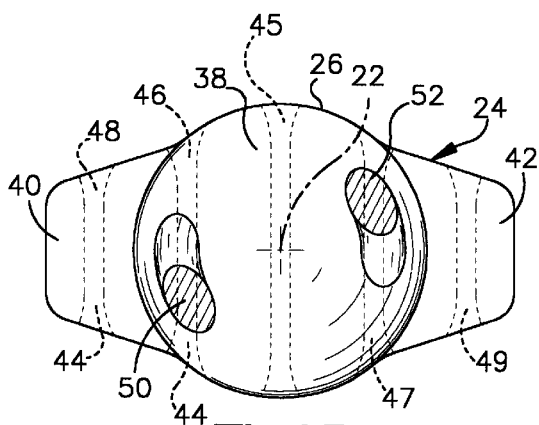
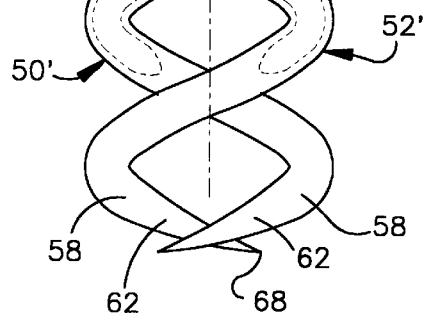
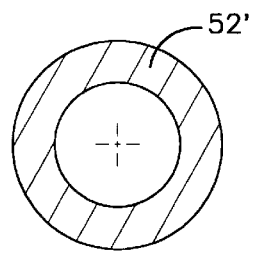
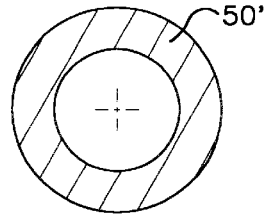
Fig.24
Fig.25
Fig.27
Fig.26

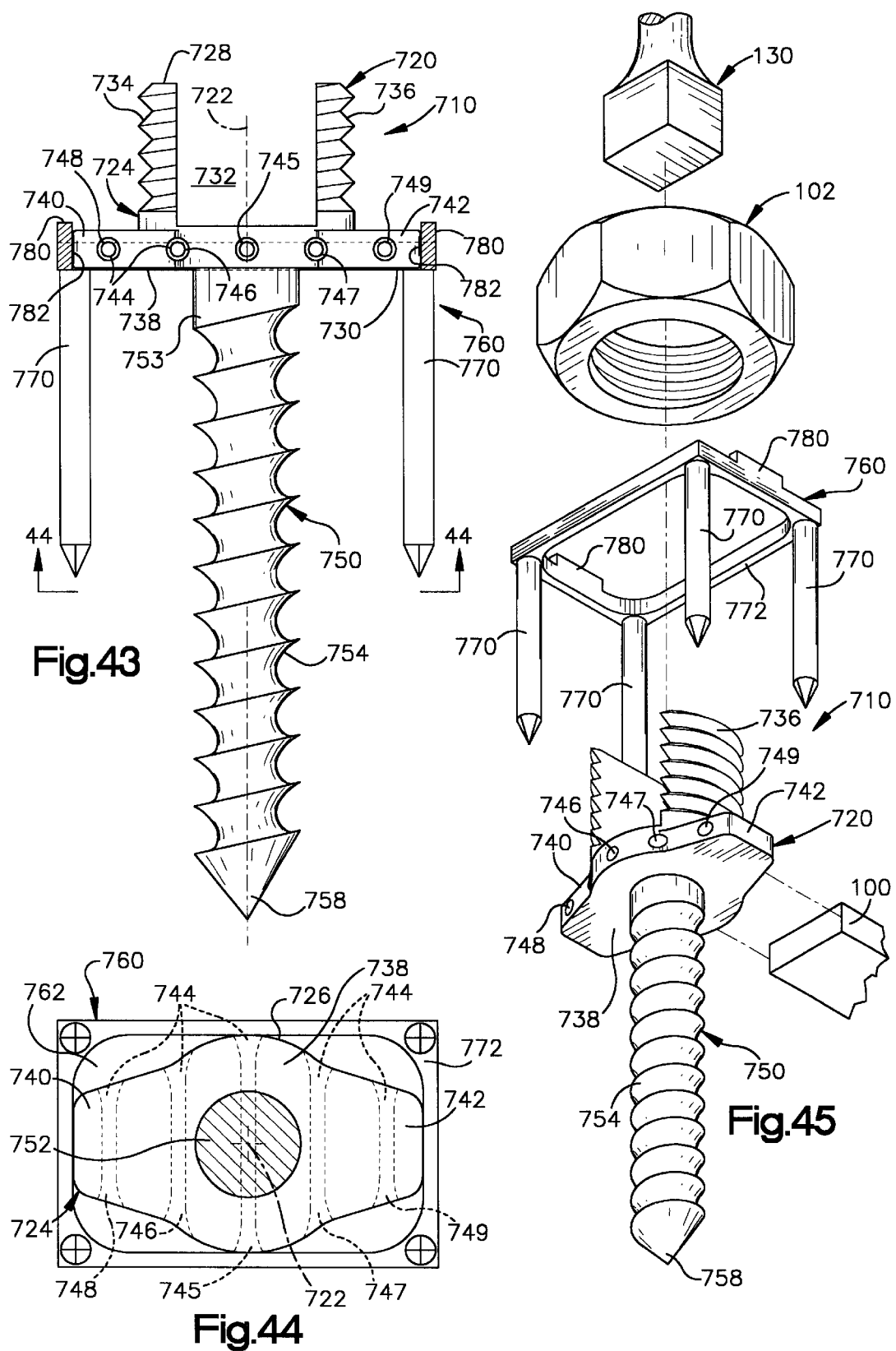

METHOD AND APPARATUS FOR CORRECTING SPINAL DEFORMITY

RELATED APPLICATIONS

This application is a continuation-in-part of co-pending U.S. patent application Ser. No. 09/812,085, filed Mar. 19, 2001, which is itself a continuation-in-part of co-pending U.S. patent application Ser. No. 09/781,847, filed Feb. 14, 2001, which is itself a continuation-in-part of co-pending U.S. patent application Ser. No. 09/708,940, filed Nov. 8, 2000, and Ser. No. 09/708,292, filed Nov. 8, 2000, now U.S. Pat. No. 6,468,309. The entire subject matter of the aforementioned four co-pending applications is incorporated herein by reference.

TECHNICAL FIELD

The present invention is directed to a method and apparatus for correcting a spinal deformity, such as scoliosis, kyphosis, and/or lordosis.

BACKGROUND OF THE INVENTION

A wide variety of instrumentation and methods for use thereof are known for the correction of spinal deformities, such as scoliosis, kyphosis, and lordosis. Many of the known instruments utilize bone screws, also referred as bone anchors, that are implanted into vertebrae. Once implanted, the bone screws are used to mount suitable spinal fixation instrumentation, such as clamps, rods, and plates. Such spinal instrumentation is then used to achieve and maintain correction of the spinal deformity and stabilize the corrected vertebrae while the vertebrae fuse together.

Most known bone screws use a conventional screw design, i.e. a solid shank, with one or more external thread convolutions. The solid shank and external threads of the conventional bone screws can cause the bone screws to displace an undesirably large amount of bone when implanted. Such conventional bone screws typically require a large amount of torque to implant the screw into a vertebral body. Furthermore, the resistance of the conventional screw to being pulled axially from the bone is dependent upon the surface area of the bone that interfaces with the screw threads.

It is also known to use a corkscrew-style helical spike as a tissue anchor. The known corkscrew-style tissue anchors, when implanted, displace less bone than the conventional bone screws, but are generally not able to withstand high tensile loads without structural failure. European Patent No. 0 374 088 A1 discloses a bone screw having a twin-corkscrew design. In this twin-corkscrew design, which is formed by drilling a passage up through a screw having a solid shank and then machining out the material between the two corkscrews, the junction of the corkscrews with the shank is unlikely to be capable of structurally withstanding high tensile loads and repetitive fatigue loads. This structural weakness in the design of the screw in the EP 0 374 088 document is further compounded by the corkscrews having a larger overall diameter than the head of the screw where torque is applied.

One of the more challenging applications of a bone screw is implantation of the screw into the cancellous bone of a vertebral body. Unfortunately, many of the known bone screws, such as those described above, can be susceptible to toggling in the vertebral body and can also pull out of the vertebral body due to the substantial forces on the screws from human body movement and muscle memory. In order to achieve a high pull-out resistance, it is common to use additional screws, which results in an undesirably large amount of bone being displaced. Alternatively, in order to achieve a high pull-out resistance, it is also known to thread a bone screw all of the way through a vertebrae and place a nut on the opposite side. However, use of such a nut increases the complexity of the surgical procedure.

As mentioned above, implanted bone screws are typically used to mount spinal fixation instrumentation, which is then used to achieve and maintain correction of a spinal deformity, such as scoliosis. Various methods and associated fixation instrumentation are known for achieving correction of a spinal deformity, but most are limited by the relatively low pull-out resistance of the known bone screws. New methods and new spinal instrumentation for achieving correction of a spinal deformity would be possible if screws with a higher pull-out resistance were available.

Hence, it is desirable to provide an apparatus for implantation into vertebrae in a minimally invasive endoscopic procedure with a reduced amount of insertion torque required. The desirable apparatus would, when implanted, be highly resistant to toggling in the vertebrae and to being pulled out of the vertebrae despite the substantial forces on the apparatus from human body movement and muscle memory. Further, the desirable apparatus could enable, and even include, new spinal instrumentation and methods for correcting spinal deformity.

SUMMARY OF THE INVENTION

The present invention provides an apparatus for correcting spinal deformity. The apparatus comprises at least one anchor for implantation into a vertebral body. The at least one anchor, when implanted, is resistant to toggling in the vertebral body and to being pulled from the vertebral body. The at least one anchor includes a platform having a first surface for facing the vertebral body. The platform includes at least one passage extending transversely through the platform. The at least one passage is for receiving a cable connected with another vertebral body. The at least one anchor further includes at least one helical spike for embedding into the vertebral body upon rotation of the platform. The at least one helical spike projects from the first surface on the platform and extends around a longitudinal axis. The at least one helical spike has a tip portion at a distal end which penetrates into the vertebral body as the platform is rotated.

In accordance with another feature of the present invention, an apparatus for correcting spinal deformity is provided. The apparatus comprises first and second anchors for implantation into first and second vertebral bodies, respectively. The anchors, when implanted, are resistant to toggling in the vertebral bodies and to being pulled from the vertebral bodies. Each of the first and second anchors includes a platform having at least one passage extending transversely through the platform. Each of the first and second anchors further includes screw means for embedding into one of the vertebral bodies upon rotation of the platform. The screw means projects from the platform on each of the first and second anchors and has a tip portion at a distal end which penetrates into a respective one of the vertebral bodies as the platform is rotated. At least one cable extends through the at least one passage in the platform on each of the first and second anchors. The at least one cable is tensionable to cause relative movement between the first and second vertebral bodies.

In accordance with yet another feature of the present invention, an apparatus for correcting spinal deformity is provided. The apparatus comprises at least two anchors for implantation into separate vertebral bodies, respectively. The at least two anchors, when implanted, are resistant to toggling in the vertebral bodies and to being pulled from the vertebral bodies. Each of the at least two anchors includes a platform having at least one passage extending transversely through the platform. Each of the at least two anchors further includes at least two helical spikes for embedding into one of the vertebral bodies upon rotation of the platform. The at least two helical spikes project from the platform on each of the at least two anchors and have tip portions at a distal end which penetrate into a respective one of the vertebral bodies as the platform is rotated. At least one cable extends through the at least one passage in the platform on each of the at least two anchors. The at least one cable is tensionable to cause relative movement between the vertebral bodies. A spinal fixation implant extends between and is connectable with the platform on each of the at least two anchors.

In accordance with still another feature of the present invention, a method for correcting spinal deformity is provided. According to the inventive method, at least two anchors are provided for implantation into separate vertebral bodies. Each of the at least two anchors includes a platform having at least one passage extending transversely through the platform. Each of the at least two anchors further includes screw means for embedding into one of the vertebral bodies upon rotation of the platform. The at least two anchors are embedded in the separate vertebral bodies. The at least two anchors are connected with at least one cable that extends through the at least one passage in the platform on each of the at least two anchors. The at least one cable is then tensioned to cause relative movement between the vertebral bodies.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 1 is a schematic side view of an apparatus for correcting spinal deformity in accordance with a first embodiment of the present invention;

FIG. 2 is a sectional view taken along line 2—2 in FIG. 1;

FIG. 5 is an exploded perspective view of the apparatus of FIG. 1, and also illustrates a driver for rotating the apparatus;

FIG. 8 is a schematic side view illustrating several vertebral bodies implanted with the apparatus of FIG. 1 and connected by a cable in accordance with the present invention, the vertebral bodies being shown in a first condition prior to correction;

FIG. 9 is a schematic view similar to FIG. 8 illustrating the vertebral bodies in a second condition following correction;

FIG. 10 is a schematic view similar to FIG. 9 illustrating a spinal fixation implant constructed in accordance with the present invention and connected to the apparatus in each of the vertebral bodies;

FIG. 11 is a schematic anterior view taken along line 11—11 in FIG. 10;

FIG. 19 is a schematic view similar to FIG. 18 illustrating the positions of the vertebrae following correction of the scoliosis;

FIG. 20 is a schematic side view taken along line 20—20 in FIG. 19 showing the lordosis;

FIG. 24 is a schematic side view of an apparatus for correcting spinal deformity in accordance with a second embodiment of the present invention;

FIG. 25 is a sectional view taken along line 25—25 in FIG. 24;

FIG. 26 is a sectional view taken along line 26—26 in FIG. 25;

FIG. 27 is a sectional view taken along line 27—27 in FIG. 24;

FIG. 43 is a schematic side view of an apparatus for correcting spinal deformity in accordance with a seventh embodiment of the present invention;

FIG. 44 is a sectional view taken along line 44—44 in FIG. 43;

FIG. 45 is an exploded perspective view of the apparatus of FIG. 43, and also illustrates a driver for rotating the apparatus.

DESCRIPTION OF EMBODIMENTS

Figure 6:
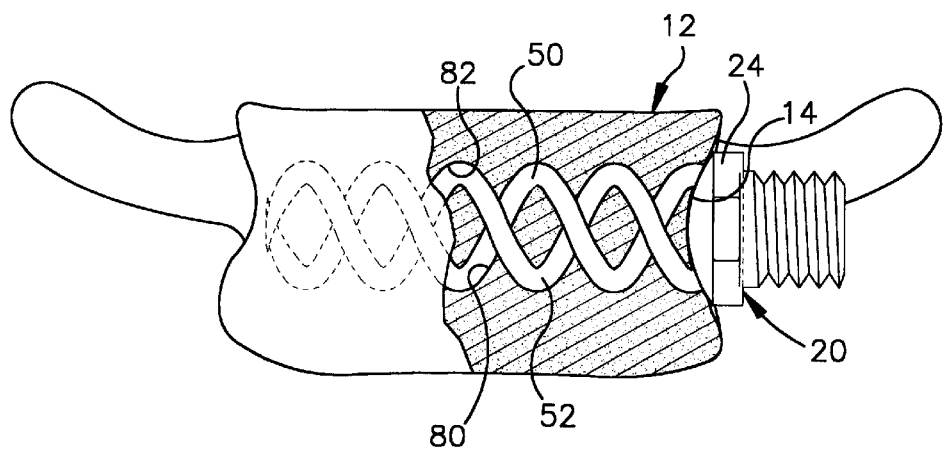
FIG. 6 is a schematic anterior view illustrating the apparatus of FIG. 1 implanted in a vertebrae.

The present invention is directed to a method and apparatus 10 for correcting spinal deformity, such as scoliosis, kyphosis, and/or lordosis. As illustrated in FIG. 1, the apparatus 10 includes an anchor 20 for implanting in a vertebrae 12 (FIG. 6). The anchor 20 is made from a biocompatible material, such as titanium or stainless steel. It is contemplated that the biocompatible material used for the anchor 20 could also be polymeric or composite (i.e., carbon fiber or other biologic composite) in nature.

The anchor 20 is centered about a longitudinal axis 22 (FIG. 1). The anchor 20 includes a platform 24 having a cylindrical outer surface portion 26 extending between oppositely disposed first and second axial ends 28 and 30 of the platform. The platform 24 includes a generally rectangular slot 32 that extends axially from the first end 28 toward the second end 30 of the platform. Adjacent the first end 28, the outer surface 26 of the platform 24 includes first and second segments of external threads 34 and 36 that are separated by the slot 32. The slot 32 and the threads 34 and 36 provide structure for connecting spinal fixation instrumentation to the platform 24 as discussed further below.

The platform 24 further includes oppositely disposed first and second wing sections 40 and 42 and a plurality of parallel passages 44. The wing sections 40 and 42 extend radially outward from the cylindrical outer surface 26 of the platform 24. As best seen in FIG. 2, each of the passages 44 extends transverse to the axis 22 and is chamfered on both of its ends. In the illustrated embodiment, a centrally located first passage 45 extends through the axis 22. Second and third passages 46 and 47 are located on either side of the centrally located first passage 45. Finally, fourth and fifth passages 48 and 49 are located in the first and second wing sections 40 and 42, respectively. It should be understood that the platform 24 could have more or less than five passages 44.

The second end 30 of the platform 24 includes an end surface 38 having a convex shape that is complimentary to the shape of a concave side surface 14 (FIG. 6) on the vertebrae 12. It should be understood that the end surface 38 of the platform 24 could be any shape necessary to remain complimentary to the shape of the side surface 14 of the vertebrae 12. The end surface 38 of the platform 24 may include barbs (not shown) or other suitable structure for fixedly engaging the side surface 14 of the vertebrae 12. Further the end surface 38 of the platform 24 may also be porous, pitted, or have a biocompatible surface coating to assist with fixation of the anchor 20 to the vertebrae 12.

Figure 3A:
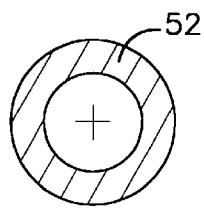
FIG. 3A is a view similar to FIG. 3 illustrating an alternate configuration.
Figure 4A:
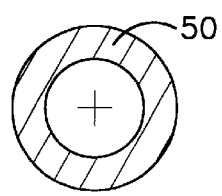
FIG. 4A is a view similar to FIG. 4 illustrating an alternate configuration.
Figure 3:
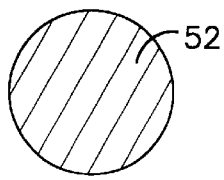
FIG. 3 is a sectional view taken along line 3—3 in FIG. 1.
Figure 4:
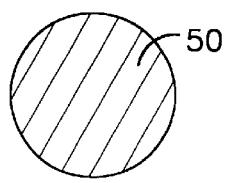
FIG. 4 is a sectional view taken along line 4—4 in FIG. 1.

First and second helical spikes 50 and 52 project tangentially from the end surface 38 of the platform 24. The helical spikes 50 and 52 resemble a pair of intertwined corkscrews. As shown in FIGS. 3 and 4, each of the helical spikes 50 and 52 has a solid cross-section. Alternatively, each of the helical spikes 50 and 52 could have a tubular cross-section, as illustrated in FIGS. 3A and 4A, which provides a means for matching the modulus of elasticity of the bone. It is contemplated that, with a tubular cross-section, the wall thickness can be varied/selected to match the modulus of elasticity of the bone, which can improve fixation strength and load-sharing characteristics of the anchor 20 and the bone.

The first and second helical spikes 50 and 52 extend around the axis 22. The spikes 50 and 52 extend in a helical pattern about the axis 22 at the same, constant radius R1. It is contemplated, however, that the first and second helical spikes 50 and 52 could extend about the axis 22 at different radiuses. Further, it is contemplated that the radius of one or both of the first and second helical spikes 50 and 52 could increase or decrease as the helical spikes extend away from the platform 24.

In the illustrated embodiment, the first and second helical spikes 50 and 52 have the same axial length, and also have the same circular cross-sectional shape. It is contemplated, however, that the firsts and second helical spikes 50 and 52 could have different axial lengths. Further, it is contemplated that the helical spikes 50 and 52 could have a different cross-sectional shape, such as an oval shape. It also contemplated that the first and second helical spikes 50 and 52 could have different cross-sectional areas (i.e., one spike being thicker than the other spike). Finally, it is contemplated that the helical spikes 50 and 52 should have the same pitch, and that the pitch of the helical spikes would be selected based on the specific surgical application and quality of the bone in which the anchor 20 is to be implanted.

Each of the first and second helical spikes 50 and 52 can be divided into three portions: a connecting portion 54, an intermediate portion 56, and a tip portion 58. The connecting portion 54 of each of the helical spikes 50 and 52 is located at a proximal end 60 that adjoins the end surface 38 of the platform 24. The connection portion 54 may include barbs (not shown) for resisting pull-out of the helical spikes 50 and 52 from the vertebrae 12. According to one method for manufacturing the anchor 20, the connecting portion 54 of each of the helical spikes 50 and 52 is fixedly attached to the platform 24 by inserting, in a tangential direction, the proximal ends 60 of the helical spikes into openings (not shown) in the end surface 38 and welding the connecting portions 54 to the platform. The inserted proximal ends 60 of the helical spikes 50 and 52 help to reduce bending stresses on the helical spikes under tensile or shear loads.

Alternatively, the helical spikes 50 and 52 may be formed integrally with the platform 24, such as by casting the anchor 20. If the anchor 20 is cast, it is contemplated that a fillet (not shown) may be added at the junction of the helical spikes 50 and 52 and the platform 24 to strengthen the junction and minimize stress concentrations at the connecting portions 54. The fillet at the junction of the helical spikes 50 and 52 and the platform 24 also helps to reduce bending stresses in the connection portions 54 of the helical spikes under tensile or shear loads.

As best seen in FIG. 2, the connecting portions 54 at the proximal ends 60 of the first and second helical spikes 50 and 52 are spaced 180° apart about the axis 22 to balance the anchor 20 and evenly distribute loads on the helical spikes. The tip portion 58 of each of the helical spikes 50 and 52 is located at a distal end 62 of the helical spikes. The intermediate portion 56 of each of the helical spikes 50 and 52 extends between the tip portion 58 and the connecting portion 54.

Figure 7:
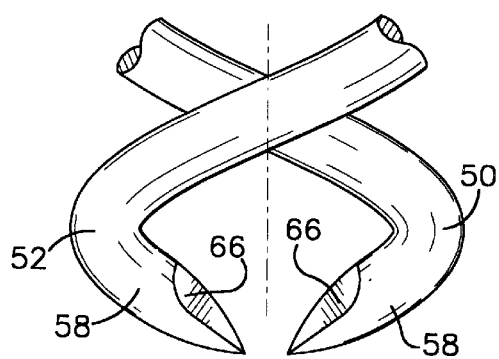
FIG. 7 illustrates an alternate configuration for an end portion of the apparatus of FIG. 1.

The tip portion 58 of each of the helical spikes 50 and 52 has an elongated conical shape with a sharp pointed tip 64 (FIG. 1) for penetrating into the vertebrae 12 as the platform 24 of the anchor 20 is rotated in a clockwise direction. FIG. 7 illustrates an alternative, self-tapping configuration for the tip portions 58 which includes a planar surface 66 for driving into the vertebrae 12, in the same manner that a wood chisel turned upside-down drives into wood, as the platform 24 is rotated. It is contemplated that the tip portions 58 could also have a pyramid shape (not shown), similar to the tip of a nail.

Although the outer surfaces of the helical spikes 50 and 52 are shown as being smooth, it is contemplated that the outer surfaces may instead be porous, pitted, or have a biocompatible coating to assist with fixation of the anchor 20 to the vertebrae 12.

It is further contemplated that the tip portions 58 of the helical spikes 50 and 52 could be covered with tip protectors (not shown) to prevent accidental sticks to surgical staff and accidental damage to tissue surrounding the vertebrae. Such tip protectors could be made of a bio-absorbable material, such as polylactic acid, or non-bio-absorbable material, such as medical grade silicon. The tip protectors would be manually removed or pushed-off during implantation of the anchor 20.

The apparatus 10 for correcting spinal deformity further includes a bar or rod 100 (FIG. 5), a lock nut 102 and a braided cable 120 (FIG. 8). The cable 120 has oppositely disposed first and second ends. The first end of the cable 120 tapers to a blunt point (not shown). The second end of the cable 120 has a fixed or permanent crimp 122. As is described in detail below, the cable is used to straighten curvature in the spine prior to attachment of the rod 100 to the anchor 20.

To implant the anchor 20, a tool (not shown) is used to punch two holes (not shown) in the cortical bone (not shown) of the vertebrae 12. The holes are punched in locations that correspond to the spacing of the tip portions 58 of the helical spikes 50 and 52 on the anchor 20. It should be noted that one or both of the configurations of the tip portions 58 illustrated in FIGS. 1–7 may be able to punch through the cortical bone upon rotation of the anchor 20, thus eliminating the need for the aforementioned tool to punch holes in the cortical bone.

The tip portions 58 are then placed in the holes in the vertebrae 12 and a rotatable driver 130 (FIG. 5) is inserted into the slot 32 in the platform 24. The driver 130 is then rotated, causing the anchor 20 to rotate as well. It is contemplated that a cylindrical sleeve (not shown) may be placed around the intermediate portions 56 and the connecting portions 54 of the helical spikes 50 and 52 to prevent the helical spikes from deforming radially outward during the initial rotation of the anchor 20.

Rotation of the anchor 20 screws the helical spikes 50 and 52 into the cancellous bone of the vertebrae 12. The tangentially-oriented connection between the connecting portions 54 of the helical spikes 50 and 52 and the platform 24 minimizes bending loads on the connecting portions during rotation of the anchor 20. Further, the tangentially-oriented connection ensures that the force vector resulting from torque and axial force applied by the driver 130 to platform 24 is transmitted along the helical centerline (not shown) of each of the helical spikes 50 and 52.

As the anchor 20 is rotated, the tip portion 58 of the first helical spike 50 penetrates the cancellous bone and cuts a first helical tunnel 80 (FIG. 6) through the vertebrae 12. Simultaneously, the tip portion 58 of the second helical spike 52 penetrates the cancellous bone of the vertebrae 12 and cuts a second helical tunnel 82. The first and second helical tunnels 80 and 82 are shaped like the helical spikes 50 and 52, respectively. Continued rotation of the anchor 20 embeds the helical spikes 50 and 52 deeper into the cancellous bone of the vertebrae 12. The anchor 20 is rotated until the convex end surface 38 of the platform 24 seats against the concave side surface 14 of the vertebrae 12 as shown in FIG. 6.

FIGS. 8–13 illustrate how the apparatus 10 is used to correct spinal deformity. Thoracic vertebrae T5–T7, indicated by reference numbers 90, 91, and 92, respectively, exhibit thoracolumbar scoliosis. After gaining access to the site anteriorly, each of the vertebrae 90–92 are implanted with the anchor 20 according to the present invention as described above. Because of the scoliosis in the spine, the anchors 20 implanted in the vertebrae 90–92 do not line up straight in the sagittal or coronal plane. Next, all disk material 94 (shown schematically in FIGS. 8–11) that normally separates each of the vertebrae 90–92 is removed.

Figure 12:
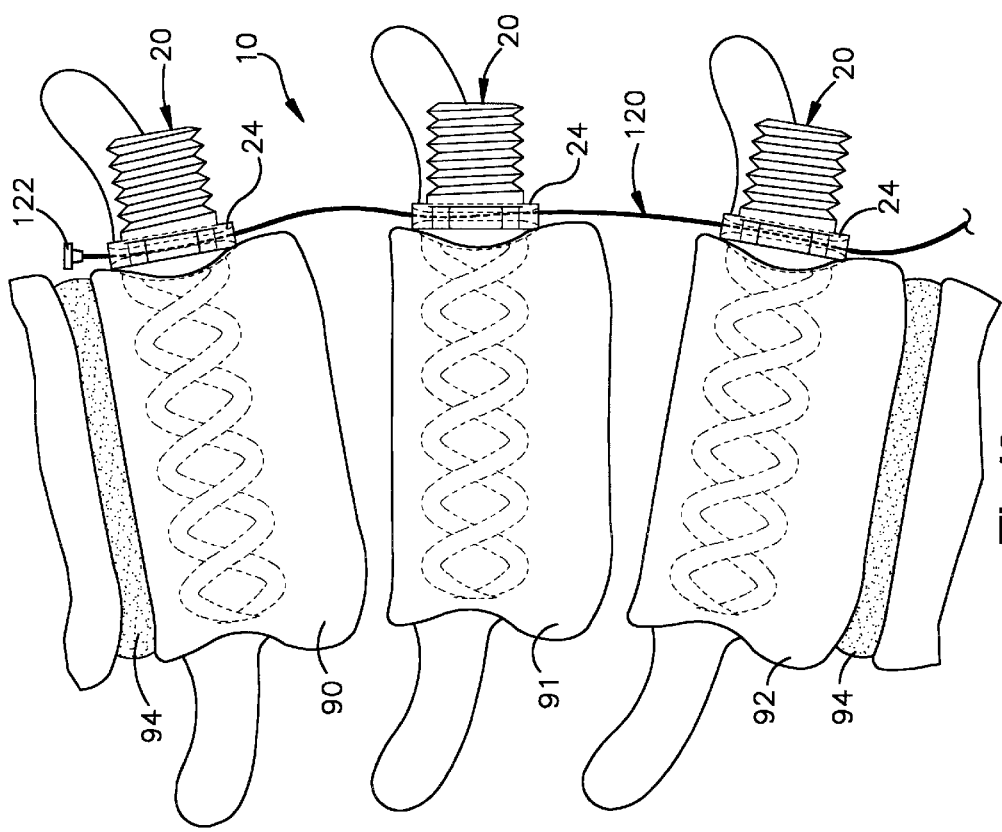
FIG. 12 is a schematic anterior view of several thoracic vertebrae in a spine having scoliosis and kyphosis, each of the vertebrae being implanted with the apparatus of FIG. 1 and connected by a cable in accordance with the present invention.

The cable 120 is passed through one of the passages 44 in the platform 24 of each of the anchors 20. More particularly, the cable 120 is threaded first through the passage 48 in the first wing section 40 of the anchor 20 implanted in the upper (as viewed in the FIGS. 8–11) vertebrae 90. Next, the cable 120 is threaded through the fifth passage 49 in the second wing section 42 of anchor 20 implanted in the middle (as viewed in the FIGS. 8–11) vertebrae 91. Finally, the cable 120 is threaded through the passage 48 in the first wing section 40 of the anchor 20 implanted in the lower (as viewed in the FIGS. 8–11) vertebrae 92. As best seen in FIGS. 8 and 12, because of the scoliosis, the cable 120 initially has a curved configuration.

The first end of the cable 120 is then pulled tight so that the crimp 122 on the second end of the cable engages the platform 24 on the anchor 20 in the upper vertebrae 90. Tension is then applied to the cable 120 in the direction of arrow A in FIGS. 8 and 12 using a cable tensioning device (not shown). The tension in the cable 120 causes the cable to straighten. As the cable 120 straightens, the middle vertebrae 91 is rotated, in the direction of arrow B, with respect to the upper and lower vertebrae 90 and 92. The rotation of the middle vertebrae 91 moves the middle vertebrae into an aligned, corrected position with respect to the upper and lower vertebrae 90 and 92, as may be seen in FIGS. 9 and 13.

Figure 13:
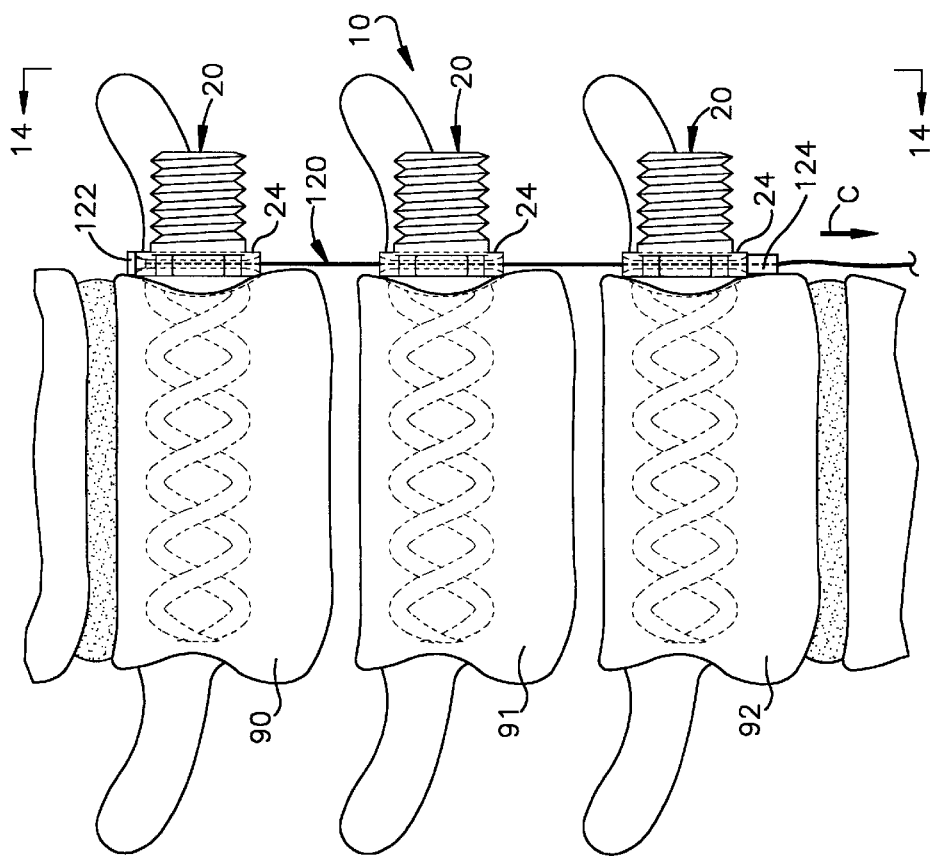
FIG. 13 is a schematic view similar to FIG. 12 illustrating the positions of the vertebrae following correction of the scoliosis.

Once the vertebrae 90–92 are in the positions shown in FIGS. 9 and 13, the rod 100 is placed into the slot 32 in each of the anchors 20. Tension is maintained in the cable 120 until the nuts 102 are screwed onto the threads 34 and 36 on each of the platforms 24 to secure the rod 100 to each of the anchors 20 (FIGS. 10 and 11). With the rod 100 secured in place, the cable is either removed or secured to the platform 24 of the anchor 20 in the lower vertebrae 92 by a crimp (not shown) or other means. Finally, the spaces left between the vertebrae 90–92 are filled with bone graft material 96 (shown schematically in FIGS. 10 and 11) that fuses the vertebrae together over time.

When implanted, the anchors 20 can be subjected to substantial forces caused by human body movement and muscle memory. In some cases, these forces can tend to pull the conventionally designed screws out of the vertebrae 90–92, and can also cause such screws to toggle in the vertebrae. However, when the helical spikes 50 and 52 of the anchors 20 are embedded in the vertebrae 90–92, the twin helical spikes of the anchors 20 provide the anchors with a high resistance to pull-out forces. Preliminary cadaver testing indicates that the anchor 20 is so resistant to being pulled axially from a vertebral body that the vertebral body itself is likely to fail before the anchor pulls out under high tensile load. Further, the helical spikes 50 and 52, and their tangential connection with the platform 24, provide the anchors 20 with a high resistance to toggling in the vertebrae 90–92.

Because the helical spikes 50 and 52 of the anchor 20 displace much less of the cancellous bone of a vertebrae during implantation than a conventional solid shank bone screw, much less torque is required to implant the anchor in a vertebrae than is required by a conventional bone screw. Finally, because the helical spikes 50 and 52 displace only a small amount of bone, the helical spikes do not create a core defect that could lead to bone deformation or failure, such as the helical spikes pulling out of the vertebrae.

Figure 15:
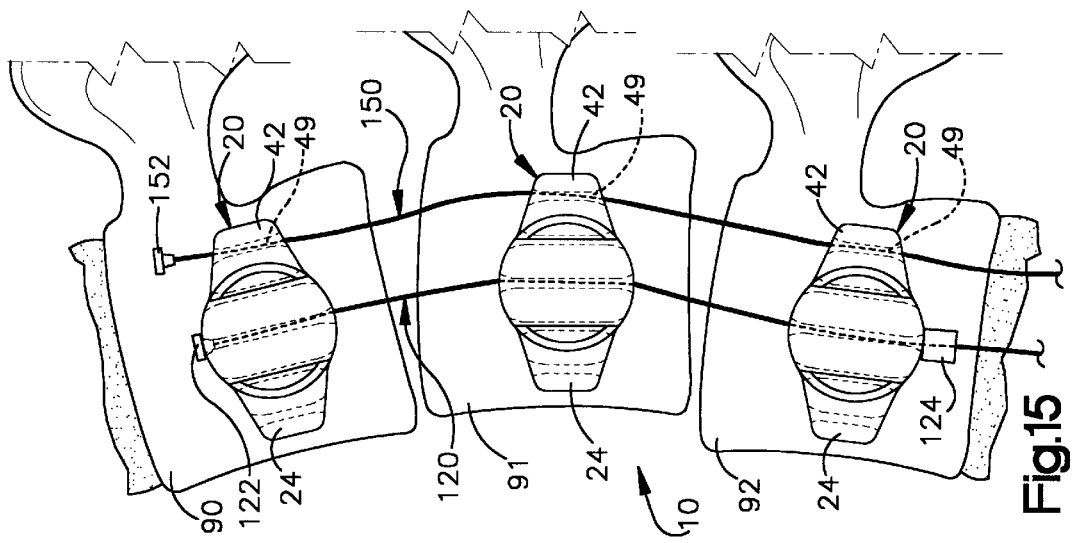
FIG. 15 is a schematic side view similar to FIG. 14 showing another cable extending between the vertebrae prior to correction of the kyphosis.

FIGS. 12–16 illustrate the thoracolumbar vertebrae 90–92 in a spine having multiple deformities, such as scoliosis and kyphosis. In accordance with another feature of the present invention, such a condition may be corrected using the apparatus 10 described above in conjunction with additional structure in the form of a secondary cable 150 (FIG. 15). In FIGS. 12–16, reference numbers that are the same as those used in FIGS. 1–11 designate parts that are the same as parts in FIGS. 1–11.

As shown in FIG. 12, the thoracic vertebrae 90–92 exhibit curvature in the coronal plane indicative of scoliosis. In order to correct the scoliosis, the anchors 20 are implanted in the vertebrae 90–92 as described above and all disk material 94 (shown schematically in the Figures) between the vertebrae 90–92 is removed.

Figure 14:
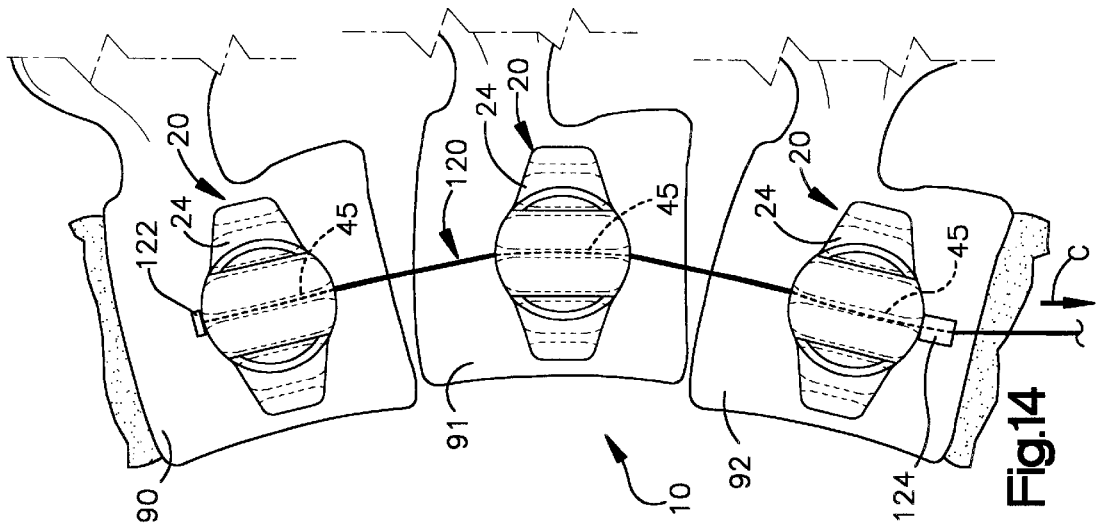
FIG. 14 is a schematic side view taken along line 14—14 in FIG. 13 showing the kyphosis.

The cable 120 is then passed through the centrally located passage 45 in the platform 24 of each of the anchors 20 as best seen in FIG. 14. The cable 120 is then pulled tight so that the crimp 122 on the second end of the cable engages the platform 24 on the anchor 20 in the upper vertebrae 90. Tension is then applied to the cable 120 in the direction of arrow C in FIG. 13. The tension in the cable 120 causes the cable to straighten. As the cable 120 straightens, the vertebrae 90–92 are moved into an aligned, corrected position shown in FIGS. 13 and 14. A locking clamp or crimp 124 is then placed on the cable at the junction of the cable and the anchor 20 in the lower vertebrae 92, thereby securing the cable to the anchors. Securing the cable 120 between the anchors 20 establishes a pivot point in the sagittal plane for movement of the vertebrae 90–92 to correct the kyphosis.

Figure 16:
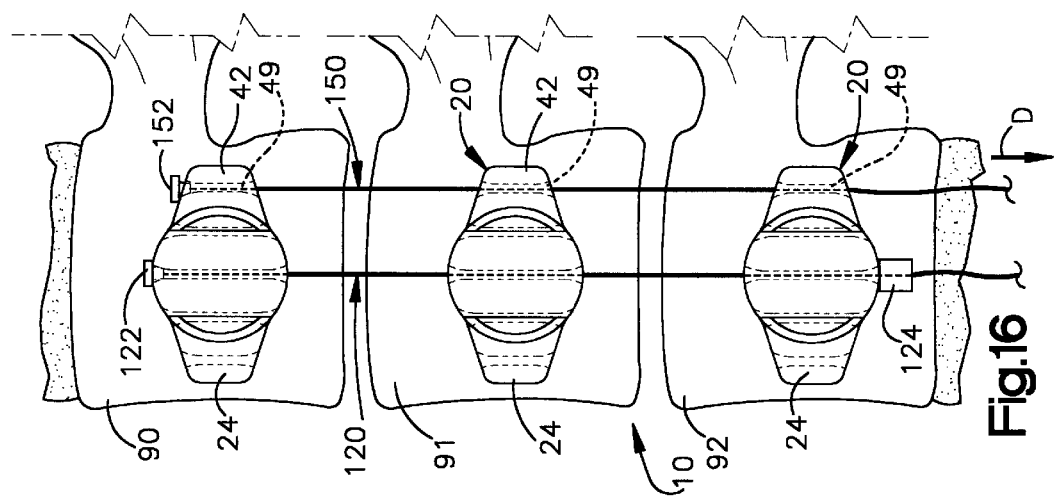
FIG. 16 is a schematic view similar to FIG. 15 illustrating the positions of the vertebrae following correction of the kyphosis.

Next, as shown in FIG. 15, the secondary cable 150 is threaded through the fifth passage 49 in the second wing section 42 of each of the anchors 20. One end of the secondary cable 150 is then pulled tight so that a crimp 152 on the other end of the secondary cable engages the platform 24 on the anchor 20 in the upper vertebrae 90, as shown in FIG. 16. Tension is then applied to the secondary cable 150 in the direction of arrow D in FIG. 16. The tension in the secondary cable 150 causes the secondary cable to straighten. As the secondary cable 150 straightens, the vertebrae 90–92 are moved, about the pivot plane formed by the cable 120, into an aligned, corrected position, as may be seen in FIG. 16.

Figure 17:
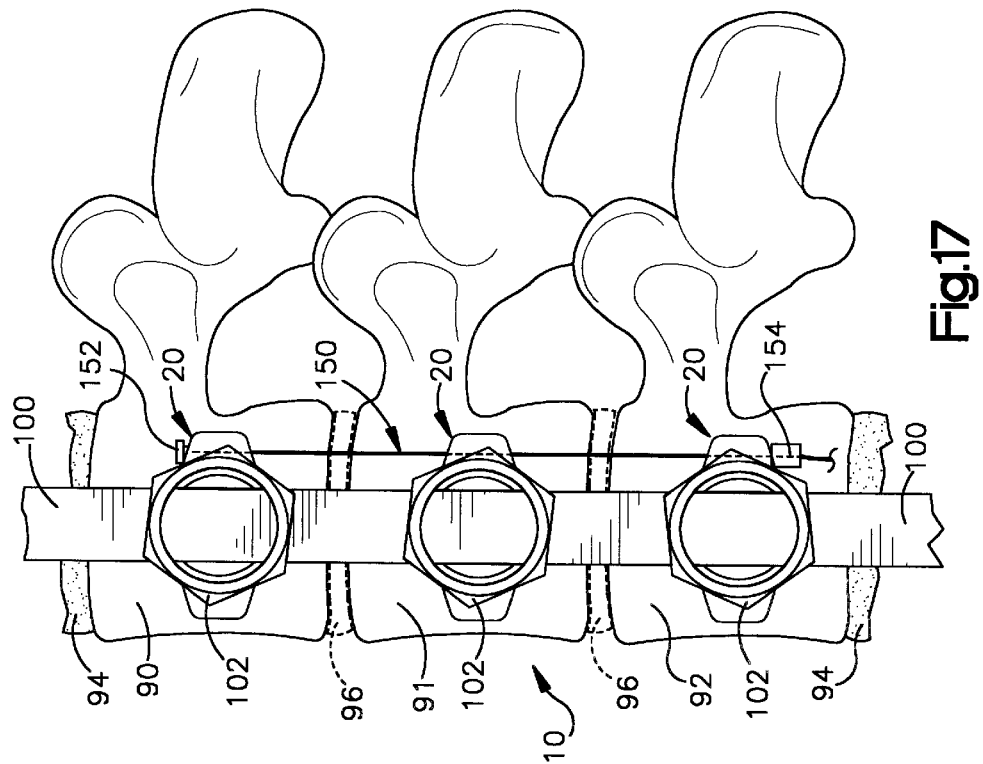
FIG. 17 is a schematic side view similar to FIG. 16 illustrating a spinal fixation implant constructed in accordance with the present invention and connected to the apparatus in each of the vertebral bodies.

Once the vertebrae 90–92 are in the positions shown in FIG. 16, the rod 100 (FIG. 17) is placed into the slot 32 in each of the anchors 20. Tension is maintained in the secondary cable 150 until the nuts 102 are screwed onto the threads 34 and 36 on each of the platforms 24 to secure the rod 100 to each of the anchors 20. With the rod 100 secured in place, the secondary cable 150 is either removed or secured to the platform 24 of the anchor 20 in the lower vertebrae 92 by a crimp 154. Finally, the spaces left between the vertebrae 90–92 are filled with the bone graft material 96 that fuses the vertebrae together over time.

Figure 21:
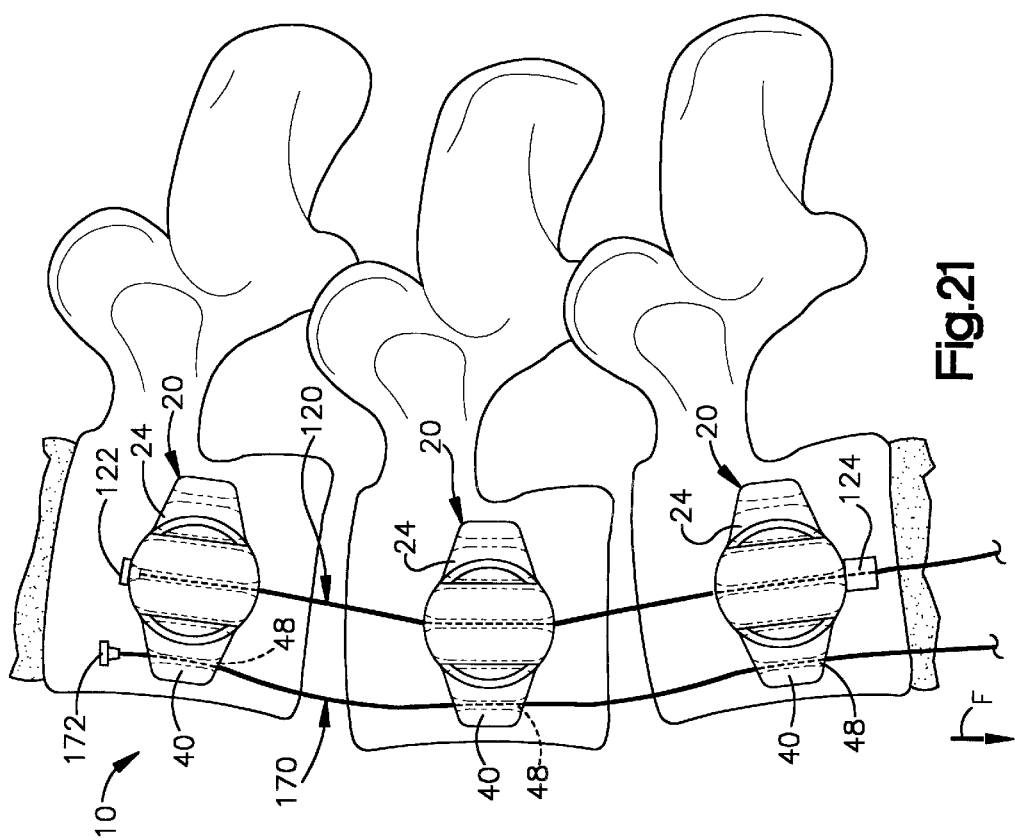
FIG. 21 is a schematic side view of the vertebrae shown in FIG. 20 and illustrating yet another cable extending between the vertebrae prior to correction of the lordosis.

FIGS. 18–23 illustrate several lumbar vertebrae in a spine having multiple deformities, such as scoliosis and lordosis. In accordance with another feature of the present invention, such a condition may be corrected using the apparatus 10 described above in conjunction with additional structure in the form of a secondary cable 170 (FIG. 21). In FIGS. 18–23, reference numbers that are the same as those used in FIGS. 1–17 designate parts that are the same as parts in FIGS. 1–17.

Figure 18:
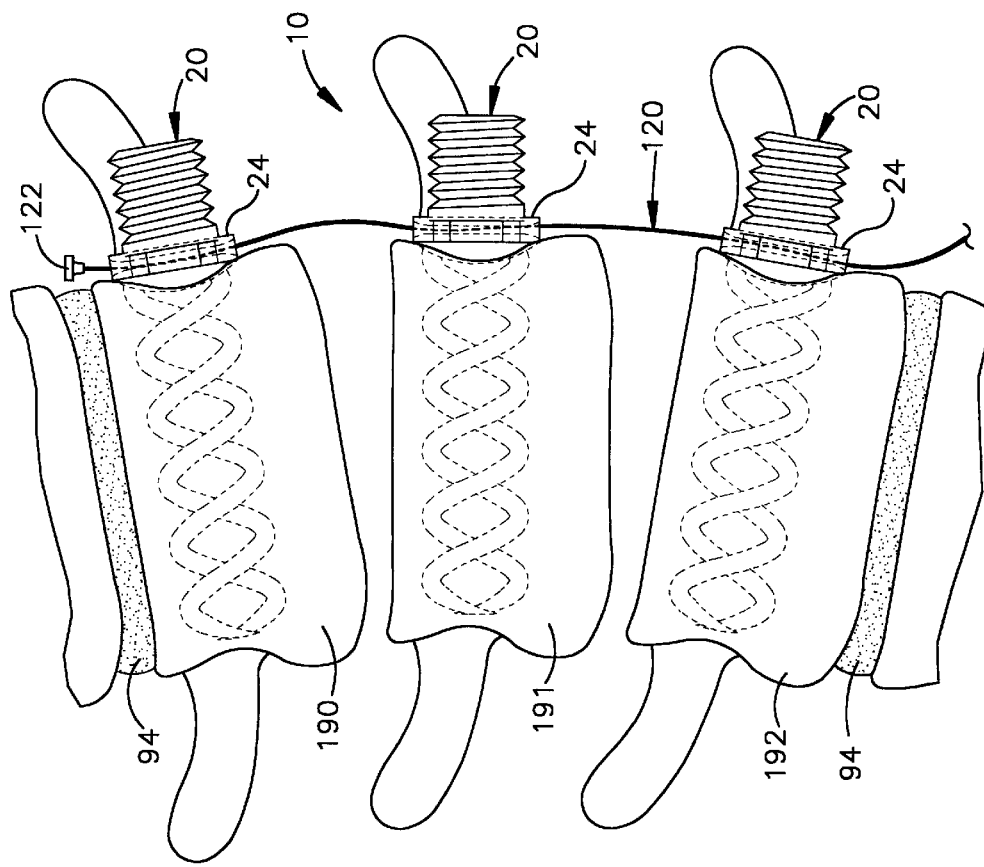
FIG. 18 is a schematic anterior view of several lumbar vertebrae in a spine having scoliosis and lordosis, each of the vertebrae being implanted with the apparatus of FIG. 1 and connected by a cable in accordance with the present invention.

As shown in FIG. 18, three lumbar vertebrae 190, 191 and 192 exhibit curvature in the coronal plane indicative of scoliosis. In order to correct the scoliosis, the anchors 20 are implanted in the vertebrae 190–192 as described above and all disk material 94 (shown schematically in the Figures) between the vertebrae is removed.

The cable 120 is then passed through the centrally located passage 45 in the platform 24 of each of the anchors 20. The cable 120 is then pulled tight so that the crimp 122 on the second end of the cable engages the platform 24 on the anchor 20 in the upper vertebrae 190. Tension is then applied to the cable in the direction of arrow E in FIG. 20. The tension in the cable 120 causes the cable to straighten. As the cable 120 straightens, the vertebrae 190–192 are moved into an aligned, corrected position shown in FIGS. 19 and 20. A locking clamp or crimp 124 is then placed on the cable at the junction of the cable and the anchor 20 in the lower (as viewed in FIG. 20) vertebrae 192, thereby securing the cable to the anchors. Securing the cable 120 between the anchors 20 establishes a pivot point in the sagittal plane for movement of the vertebrae 190–192 to correct the lordosis.

Next, as shown in FIG. 21, the secondary cable 170 is threaded through the passage 48 in the first wing section 40 of each of the anchors 20. One end of the secondary cable 170 is then pulled tight so that a crimp 172 on the other end of the secondary cable engages the platform 24 on the anchor 20 in the upper vertebrae 190. Tension is then applied to the secondary cable 170 in the direction of arrow F in FIG. 21. The tension in the secondary cable 170 causes the secondary cable to straighten. As the secondary cable 170 straightens, the vertebrae 190–192 are moved, about the pivot plane formed by the cable 120 into an aligned, corrected position, as may be seen in FIG. 22.

Figure 22:
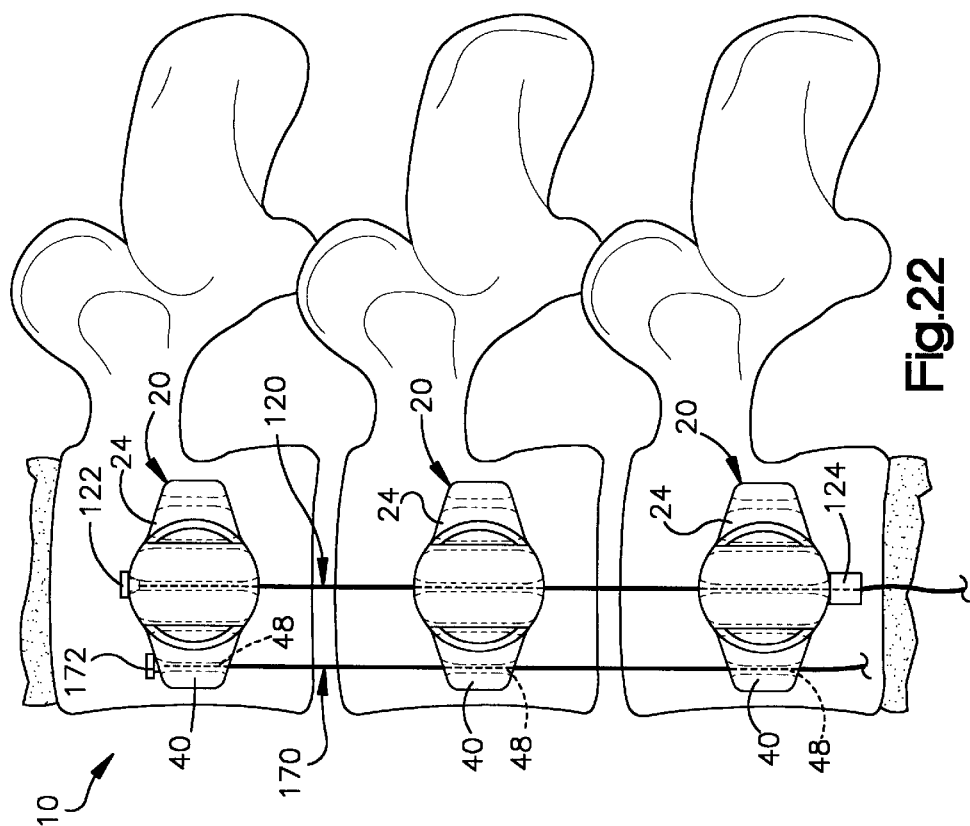
FIG. 22 is a schematic view similar to FIG. 21 illustrating the positions of the vertebrae following correction of the lordosis.
Figure 23:
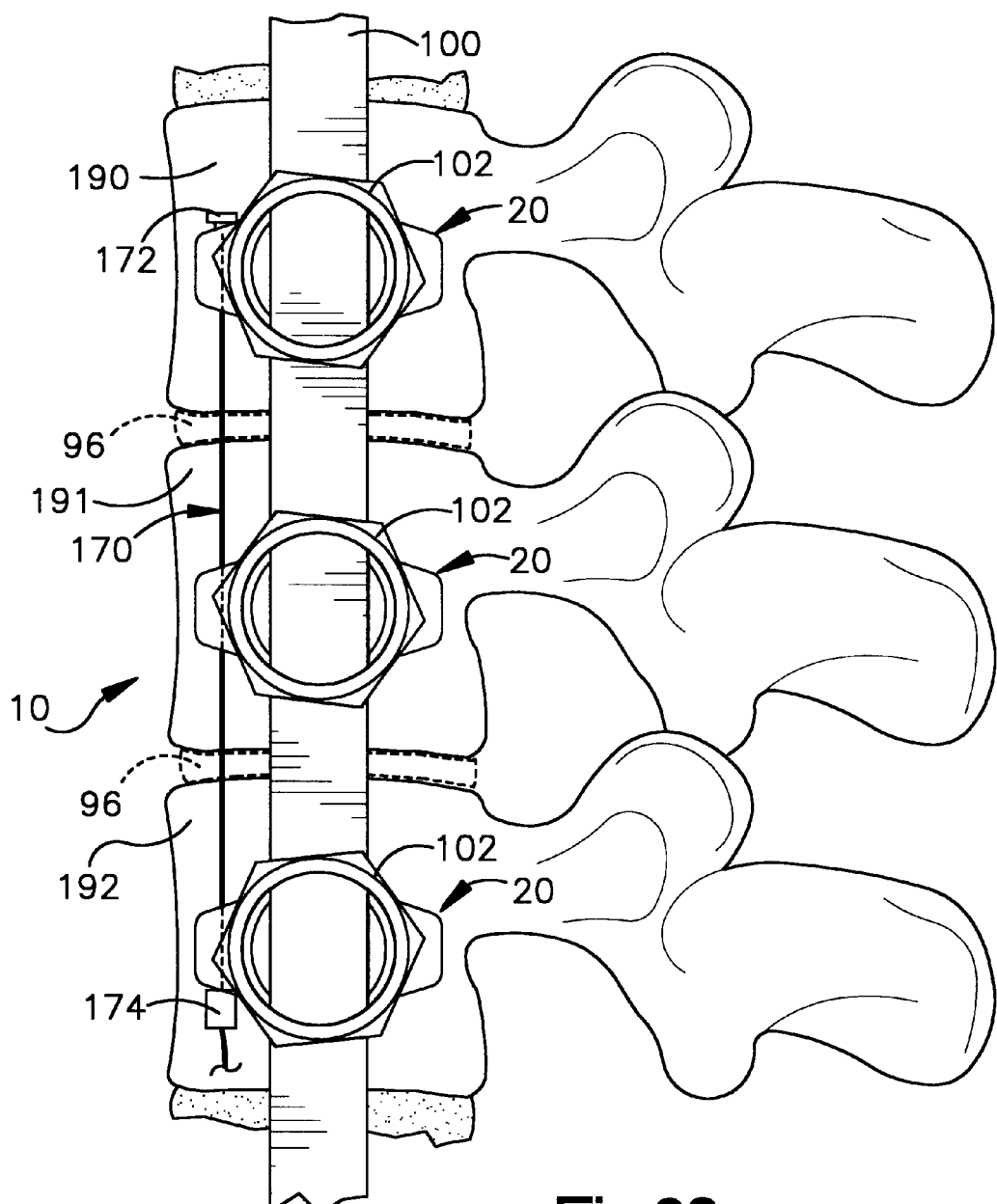
FIG. 23 is a schematic side view similar to FIG. 22 illustrating a spinal fixation implant constructed in accordance with the present invention and connected to the apparatus in each of the vertebral bodies.

Once the vertebrae 190–192 are in the positions shown in FIG. 22, the rod 100, illustrated in FIG. 23, is placed into the slot 32 in each of the anchors 20. Tension is maintained in the secondary cable 170 until the nuts 102 are screwed onto the threads 34 and 36 on each of the platforms 24 to secure the rod 100 to each of the anchors 20. With the rod 100 secured in place, the secondary cable 170 is either removed or secured to the platform 24 of the anchor 20 in the lower vertebrae 192 by a crimp. Finally, the spaces left between the vertebrae 90–92 are filled with the bone graft material 96 that fuses the vertebrae together over time.

It should be understood by those skilled in the art that by using one or more of the cables 120, 150 and 170 threaded through various combinations of the passages 45–49 in each of the anchors 20, vertebral body movement can be achieved and controlled in all three planes (sagittal, coronal, and horizontal). Hence, correction of spinal deformities in all three planes can be achieved using the apparatus 10.

FIGS. 24–27 illustrate an apparatus 210 constructed in accordance with a second embodiment of the present invention. In the second embodiment of FIGS. 24–27, reference numbers that are the same as those used in FIGS. 1–6 designate parts that are the same as parts shown in FIGS. 1–6.

According to the second embodiment, the apparatus 210 comprises an anchor 220 having helical spikes 50' and 52'. FIGS. 24–27 illustrate that the connecting portions 54 and the tip portions 58 of the helical spikes 50' and 52' have a solid cross-section, while the intermediate portions 56 have a tubular cross-section. The modified configuration of the anchor 220 provides additional means for matching the modulus of elasticity of the bone.

The anchor 220 is implantable into vertebrae in the same manner as the anchor 20 described above. Once implanted, the anchor 220 may be used along with the rod 100 and one or more of the cables described above to achieve and maintain correction of spinal deformity.

Figure 28:
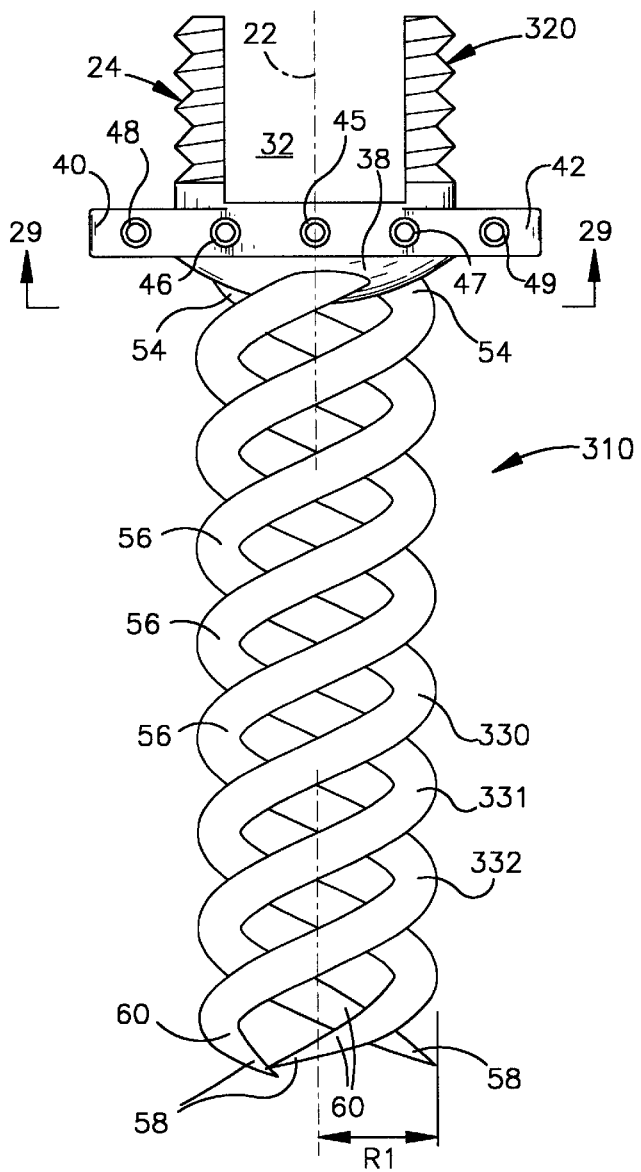
FIG. 28 is a schematic side view of an apparatus for correcting spinal deformity in accordance with a third embodiment of the present invention.
Figure 29:
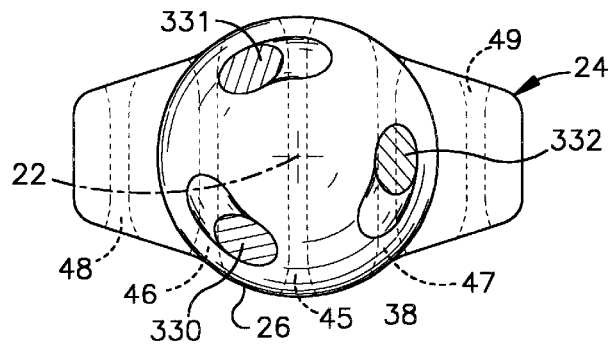
FIG. 29 is a sectional view taken along line 29—29 in FIG. 28.

FIGS. 28 and 29 illustrate an apparatus 310 constructed in accordance with a third embodiment of the present invention. In the third embodiment of FIGS. 28 and 29, reference numbers that are the same as those used in FIGS. 1–6 designate parts that are the same as parts shown in FIGS. 1–6.

According to the third embodiment, the apparatus 310 comprises an anchor 320 having three helical spikes 330, 331, and 332 projecting tangentially from the end surface 38 of the platform 24. The spikes 330–332 extend around the axis 22. As shown in FIGS. 28 and 29, each of the helical spikes 330–332 has a solid cross-section. Alternatively, each of the helical spikes 330–332 could have a tubular cross-section, which provides a means for matching the modulus of elasticity of the bone.

As shown in FIG. 29, the connecting portions 54 at the proximal ends 60 of the helical spikes 330–332 are spaced 120° apart about the axis 22, which balances the anchor 320 and evenly distributes loads on the helical spikes. Each of the three helical spikes 330–332 extends in a helical pattern about the axis 22 at the same, constant radius R1. It is contemplated, however, that one or more of the helical spikes 330–332 could extend about the axis 22 at different radiuses. Further, it is contemplated that the radius of one or more helical spikes 330–332 could increase or decrease as the helical spikes extend away from the platform 24.

The three helical spikes 330–332 have the same axial length and also have the same circular cross-sectional shape. It is contemplated, however, that one or more of the helical spikes 330–332 could have different axial lengths. Further, it is contemplated that one or more of the helical spikes 330–332 could have a different cross-sectional shape, such as an oval shape. It also contemplated that the one or more of the helical spikes 330–332 could have different cross-sectional areas (i.e., one spike being thicker or thinner than the other two spikes). Finally, it is contemplated that the helical spikes 330–332 should have the same pitch, and that the pitch of the helical spikes would be selected based on the specific surgical application and quality of the bone in which the anchor 20 is to be implanted.

It is contemplated that the modified configuration of the helical spikes 50' and 52' illustrated in the second embodiment of FIGS. 24–27 could also be applied to the third embodiment of FIGS. 28 and 29. Specifically, the connecting portions 54 and/or the tip portions 58 of the helical spikes 330–332 could have a solid cross-section, while the intermediate portions 56 have a tubular cross-section. Such modified configurations of the anchor 320 provide additional means for matching the modulus of elasticity of the bone and allow the surgeon to select a particular configuration based on the specific surgical application and quality of the bone in which the anchor is to be implanted.

The tip portion 58 of each of the helical spikes 330–332 illustrated in FIG. 28 has an elongated conical shape for penetrating into a vertebrae as the platform 24 of the anchor 320 is rotated in the clockwise direction. It should be understood that the tip portions 58 of the helical spikes 330–332 of the anchor 320 could alternatively be configured like the tip portions illustrated in FIG. 7.

It is further contemplated that the tip portions 58 of the helical spikes 330–332 could be covered with tip protectors (not shown) to prevent accidental sticks to surgical staff and accidental damage to tissue surrounding the fractured bone. Such tip protectors could be made of a bio-absorbable material, such as polylactic acid or a non-bio-absorbable material, such as medical grade silicon. The tip protectors would be manually removed or pushed-off during implantation of the anchor 320.

The anchor 320 according to the third embodiment of FIGS. 28 and 29 is implanted in a vertebrae in the same manner as the anchor 20 according to the first embodiment of FIGS. 1–6. Because the helical spikes 330–332 of the anchor 320 displace less cancellous bone during implantation than a conventional solid shank bone screw, less torque is required to implant the anchor in a vertebrae than is required by a conventional bone screw. Further, because the helical spikes 330–332 displace only a small amount of bone, the helical spikes do not create a core defect that could lead to bone destruction or failure, such as the helical spikes pulling out of the vertebrae. Finally, when implanted, the anchor 320 is highly resistant to being pulled out of the vertebrae and to toggling in the vertebrae despite being subjected to substantial forces caused by human body movement and muscle memory.

Once the anchor 320 is implanted into a vertebrae in the manner described above with regard to the first embodiment, the anchor 320 may be used along with the rod 100 and one or more of the cables described above to achieve and maintain correction of spinal deformity.

FIGS. 30–36 illustrate an apparatus 410 constructed in accordance with a fourth embodiment of the present invention. In the fourth embodiment of FIGS. 30–36, reference numbers that are the same as those used in FIGS. 1–6 designate parts that are the same as parts shown in FIGS. 1–6.

According to the fourth embodiment, the apparatus 410 comprises an anchor 420 made from a biocompatible material. Known biocompatible materials include titanium, stainless steel, and spring steel. It is contemplated that the biocompatible material used for the anchor 420 could be polymeric or composite-in nature. In accordance with one feature of the present invention, the anchor 420 is at least partially made from a shape memory alloy that is biocompatible. As is known in the art, shape memory alloys have the ability to return to a predetermined shape when heated. When a shape memory alloy is cold, or below its transition temperature range (TTR), the material has a low yield strength and can be deformed into a new shape, which it will retain until heated. However, when a shape memory alloy is heated above its TTR, the material undergoes a change in crystal structure (from a martensite structure to an austenite structure), which causes the material to return to its original, or "memorized" shape. A memorized shape is imprinted into a shape memory alloy by first holding the material in the desired shape at a high temperature, and then continuing to hold the material in the desired shape as it cools through its TTR.

Figure 30:
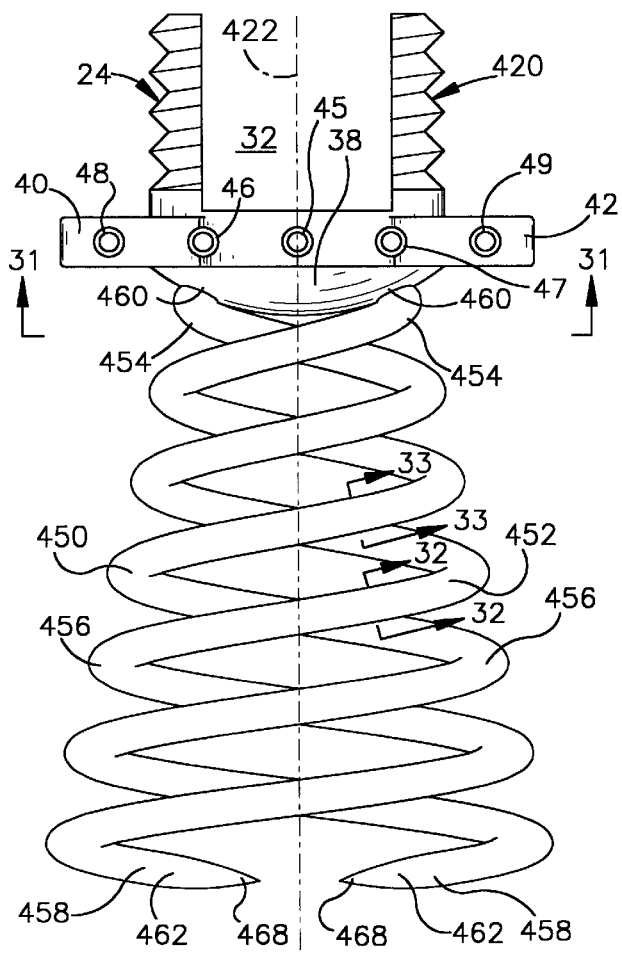
FIG. 30 is a schematic side view of an apparatus for correcting spinal deformity in accordance with a fourth embodiment of the present invention.
Figure 32:
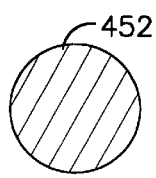
FIG. 32 is a sectional view taken along line 32—32 in FIG. 30.
Figure 32A:
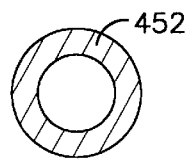
FIG. 32A is a schematic view similar to FIG. 32 illustrating an alternate configuration.
Figure 33:
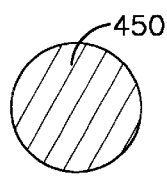
FIG. 33 is a sectional view taken along line 33—33 in FIG. 30.
Figure 33A:
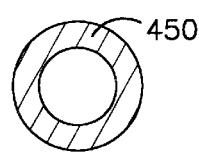
FIG. 33A is a schematic view similar to FIG. 33 illustrating an alternate configuration.

As shown in FIG. 30, the anchor 420 is centered about a longitudinal axis 422. The anchor 420 includes the platform 24 described above with regard to FIGS. 1–6. First and second helical spikes 450 and 452 project tangentially from the end surface 38 of the platform 24. The helical spikes 450 and 452 resemble a pair of intertwined corkscrews, both of which have a conical shape that increases in diameter as the helical spikes extend away from the platform 24. As shown in FIGS. 32 and 33, each of the helical spikes 450 and 452 has a solid cross-section. Alternatively, each of the helical spikes 450 and 452 could have a tubular cross-section, as illustrated in FIGS. 32A and 33A, which provides a means for matching the modulus of elasticity of the bone.

According to the fourth embodiment illustrated in FIGS. 30–36, the first and second helical spikes 450 and 452 extend symmetrically in a conical pattern about the axis 422. It is contemplated, however, that the conical shape of the first and second helical spikes 450 and 452 could be different from each other (i.e., one spike being a smaller cone than the other spike).

As shown in FIGS. 30–36, the first and second helical spikes 450 and 452 have the same axial length, and also have the same cross-sectional shape. It is contemplated, however, that the first and second helical spikes 450 and 452 could have different axial lengths. Further, it is contemplated that the helical spikes 450 and 452 could have a different cross-sectional shape, such as an oval shape. It also contemplated that the first and second helical spikes 450 and 452 could have different diameters (i.e., one spike being thicker than the other spike). Finally, it is contemplated that the helical spikes 450 and 452 should have the same pitch, and that the pitch of the helical spikes would be selected based on the specific surgical application and quality of the bone in which the anchor 420 is to be implanted.

Each of the first and second helical spikes 450 and 452 can be divided into three portions: a connecting portion 454, an intermediate portion 456, and a tip portion 458. The connecting portion 454 of each of the helical spikes 450 and 452 is located at a proximal end 460 that adjoins the end surface 38 of the platform 24. The connecting portion 454 may include barbs (not shown) for resisting pull-out of the helical spikes 450 and 452 from a vertebrae. According to one method for manufacturing the anchor 420, the connecting portion 454 of each of the helical spikes 450 and 452 is fixedly attached to the platform 24 by inserting, in a tangential direction, the proximal ends 460 of the helical spikes into openings (not shown) in the end surface 38 and welding the connecting portions 454 to the platform. The inserted proximal ends 460 of the helical spikes 450 and 452 help to reduce bending stresses on the helical spikes under tensile or shear loads.

Figure 31:
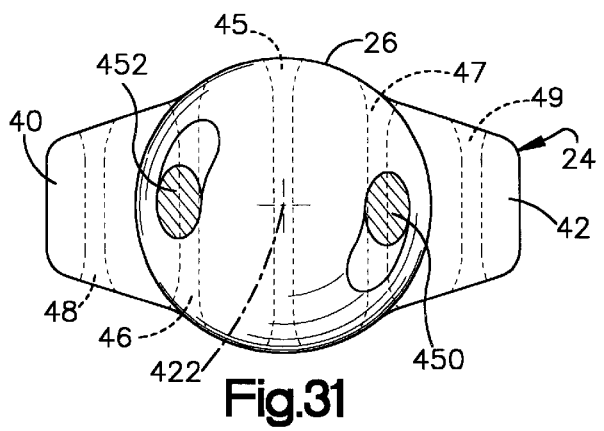
FIG. 31 is a sectional view taken along line 31—31 in FIG. 30.

Alternatively, the helical spikes 450 and 452 may be formed integrally with the platform 24, such as by casting the anchor 420. If the anchor 420 is cast, it is contemplated that a fillet (not shown) may be added at the junction of the helical spikes 450 and 452 and the platform 24 to strengthen the junction and minimize stress concentrations at the connecting portions 454. The fillet at the junction of the helical spikes 450 and 452 and the platform 24 also helps to reduce bending stresses in the connection portions 454 of the helical spikes under tensile or shear loads. As best seen in FIG. 31, the connecting portions 454 at the proximal ends 460 of the first and second helical spikes 450 and 452 are spaced 180° apart about the axis 422 to balance the anchor 420 and evenly distribute loads on the helical spikes.

The tip portion 458 of each of the helical spikes 450 and 452 is located at a distal end 462 of the helical spikes. The intermediate portion 456 of each of the helical spikes 450 and 452 extends between the tip portion 458 and the connecting portion 454. The intermediate portion 456 and the tip portion 458 of each of the helical spikes 450 and 452 have a diameter that is less than or equal to the diameter of the connecting portions 454. If the diameter of the intermediate portion 456 and the tip portion 458 is less than the diameter of the connecting portion 454 of each of the helical spikes 450 and 452, the increased thickness of the connecting portions will help to provide the anchor 420 with increased tensile strength at the junction of the helical spikes and the platform 24.

The tip portion 458 of each of the helical spikes 450 and 452 has an elongated conical shape with a sharp pointed tip 468 for penetrating into a vertebrae as the platform 24 of the anchor 420 is rotated in a clockwise direction. It should be understood that the tip portions 458 could alternatively have the configuration shown in FIG. 7. It is contemplated that the tip portions 458 could also have a pyramid shape (not shown), similar to the tip of a nail. Although the outer surfaces of the helical spikes 450 and 452 are shown as being relatively smooth in FIGS. 30–36, it is contemplated that the outer surfaces may instead be porous, pitted, or have a biocompatible coating to assist with fixation of the anchor 420 to a vertebrae.

Figure 36:
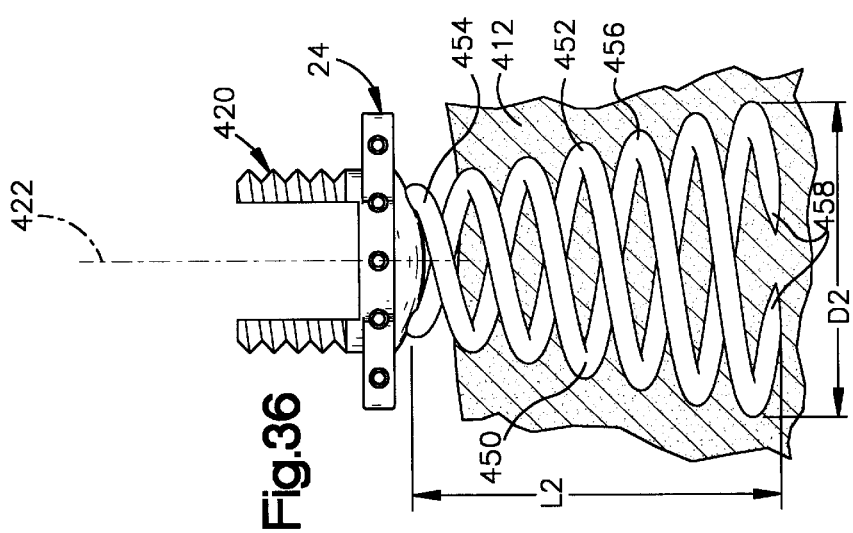
FIG. 36 is a schematic view similar to FIG. 34 illustrating the apparatus of FIG. 30 in a second condition following implantation in the vertebrae.
Figure 35:
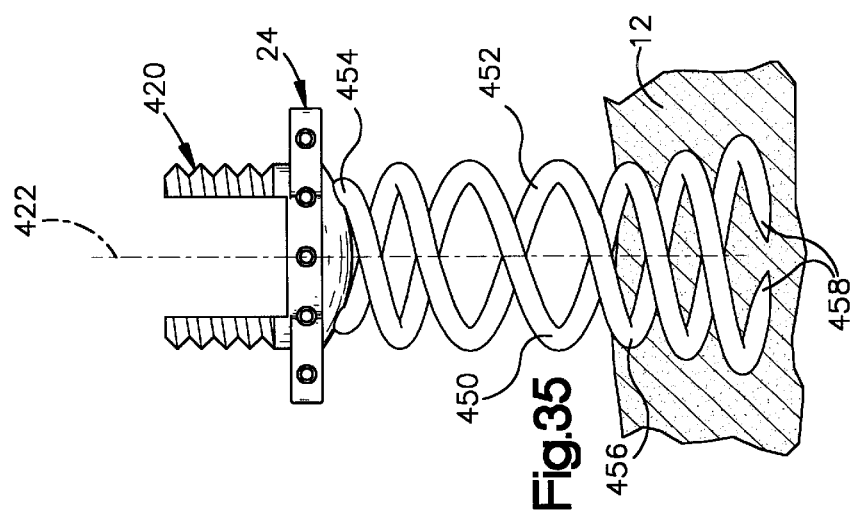
FIG. 35 is a schematic view similar to FIG. 34 illustrating the apparatus of FIG. 30 during implantation in the vertebrae.
Figure 34:
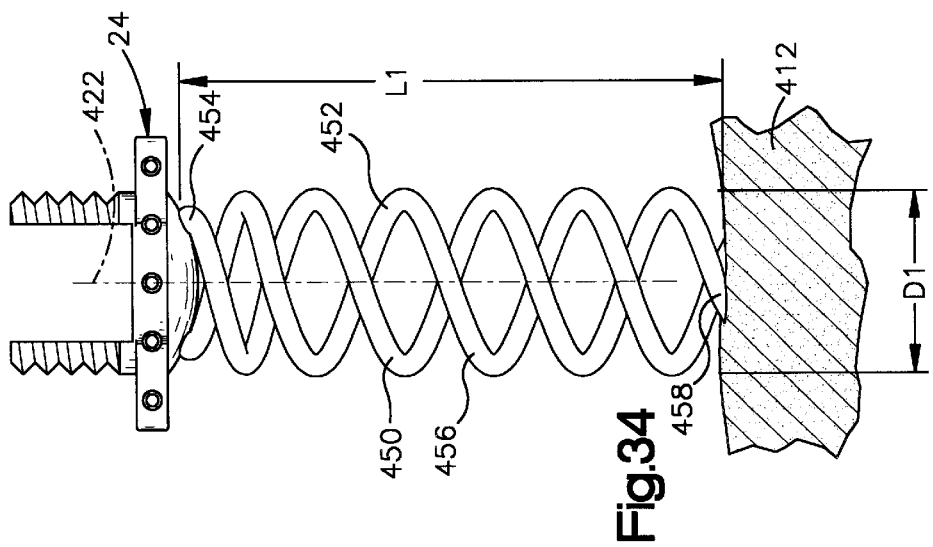
FIG. 34 is a schematic side view, partially in section, illustrating the apparatus of FIG. 30 in a first condition prior to implantation in a vertebrae.

As mentioned previously, the anchor 420 is made from a shape memory alloy, which allows the anchor to have more than one shape. FIGS. 34–36 illustrate the shapes of the anchor 420 at various stages of the implantation process. The shape that is "memorized" into the material of the anchor 420 is illustrated in FIGS. 30 and 36. FIG. 34 illustrates the anchor 420 in a first condition prior to implantation in a vertebrae 412. In the first condition, the helical spikes 450 and 452 of the anchor 420 do not have a conical shape, but instead have a generally cylindrical shape with a uniform maximum diameter D1. Further, in the first condition, the helical spikes 450 and 452 have an axial length L1. In order for the anchor 420 to take the shape of the first condition, the temperature of the anchor must be below its TTR so that the material of the anchor is soft and ductile.

FIG. 35 illustrates the anchor 420 during implantation into the vertebrae 412. During implantation, it is desirable for the helical spikes to return to the memorized conical shape of FIG. 30. To return the helical spikes 450 and 452 to the conical shape, heat is applied to the anchor 420 until the temperature of the anchor exceeds the TTR for the shape memory material. Simple body temperature may be sufficient to raise the temperature of the anchor 420 above its TTR. If additional heat is needed, heat may be applied in many ways, such as passing electric current through a wire connected with the anchor 420, transmitting radio waves that inductively heat the anchor, or applying a hot saline pack to the anchor.

With the helical spikes 450 and 452 expanding radially, but contracting axially, due to the heat being applied, the helical spikes are implanted in the vertebrae 412 in the conical shape, or second condition, illustrated in FIG. 36. As shown in FIG. 36, in the implanted second condition, the helical spikes 450 and 452 have a maximum diameter D2 that is larger than the maximum diameter D1 of the helical spikes in the first condition. Further, in the implanted second condition, the helical spikes 450 and 452 have an axial length L2 that is smaller than the axial length of the helical spikes in the first condition.

It is contemplated that the first and second conditions of the helical spikes 450 and 452 described above could be achieved even if only certain portions of the helical spikes were made from a shape memory alloy. For example, it is contemplated that the tip portions 458 and the intermediate portions 456 of the helical spikes 450 and 452 could be made from a shape memory alloy, while the connecting portions 454 are made from another biocompatible metal. Further, it should be understood that if a shape memory material is not used at all in the helical spikes 450 and 452 and a material such as spring steel is used instead, the helical spikes would still be able to be compressed in to the first condition of FIG. 34, and expand into the second condition upon implantation as shown in FIGS. 35 and 36.

The anchor 420 is implantable into vertebrae in the same manner as the anchor 20 described above with regard to FIGS. 1–6. When implanted, the anchor 420 can be subjected to substantial forces caused by human body movement and muscle memory. In some cases, these forces can tend to pull the known screws used in such an application out of a vertebrae or can cause the screws to toggle in the vertebrae. However, when the helical spikes 450 and 452 are embedded in a vertebrae, the conical shape of the two helical spikes of the anchors 420 provides the anchors with a high resistance to pull-out forces and a high resistance to toggling in the vertebrae. The conical shape of the helical spikes 450 and 452 increases the amount of surface area engaged by the anchor 420, distributes any load on the anchor, and provides fixation over a larger volume of bone. Finally, the use of a shape memory alloy for the helical spikes 450 and 452 allows the anchor 420 to have a smaller diameter prior to implantation, which permits minimally invasive endoscopic surgery through a cannula, and a wider diameter when implanted.

Because the helical spikes 450 and 452 of the anchor 420 displace much less of the cancellous bone of a vertebrae during implantation than a conventional solid shank bone screw, much less torque is required to implant the anchor in the vertebrae than is required by a conventional bone screw. Further, because the helical spikes 450 and 452 displace only a small amount of bone, the helical spikes do not create a core defect that could lead to bone deformation or failure, such as the helical spikes pulling out of the vertebrae. Advantageously, the conical shape of the helical spikes 450 and 452 increases the amount of surface area engaged by the anchor 420, spreads any load on the anchor out over different areas of the vertebrae 412, and provides fixation over a larger volume of bone. The aforementioned advantages of the conical shape of the helical spikes 450 and 452 is especially helpful when implanting the anchor 420 in osteoporotic bone.

Once implanted, the anchor 420 may be used along with the rod 100 and one or more of the cables described above to achieve and maintain correction of spinal deformity.

Figure 37:
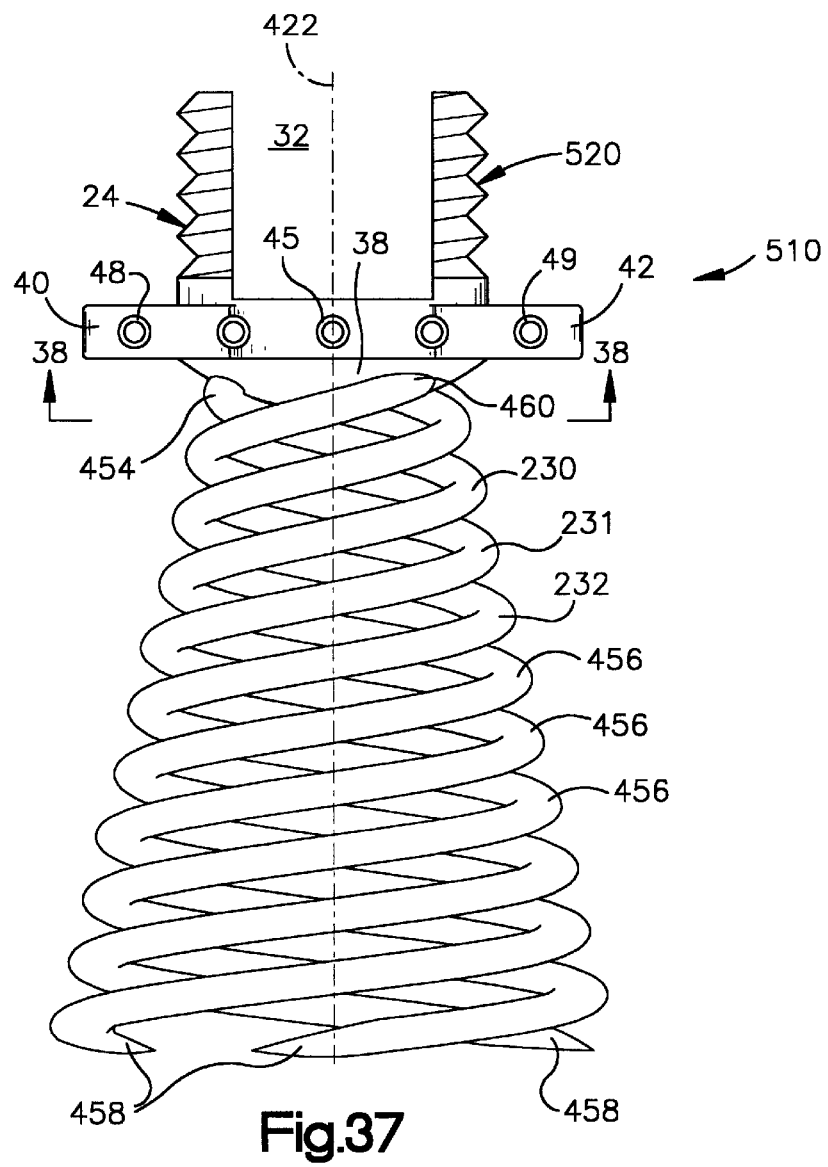
FIG. 37 is a schematic side view of an apparatus for correcting spinal deformity in accordance with a fifth embodiment of the present invention.
Figure 38:
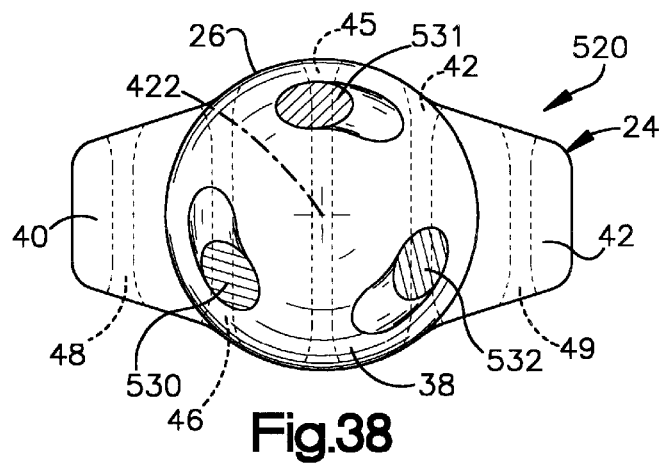
FIG. 38 is a sectional view taken along line 38—38 in FIG. 37.
Figure 39:
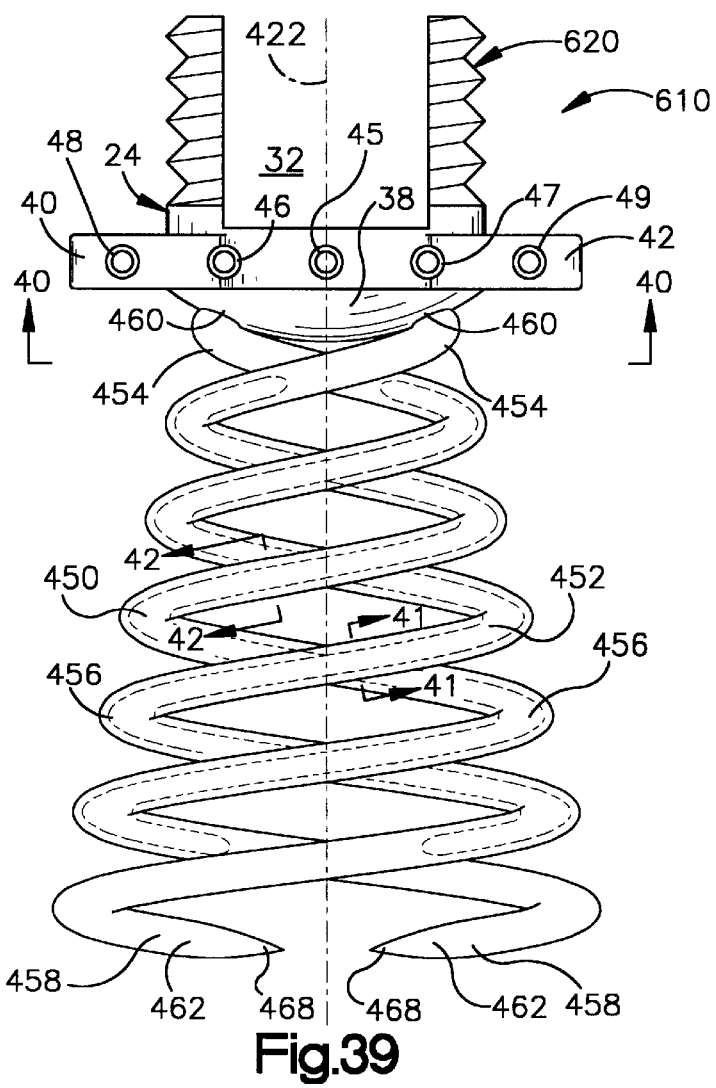
FIG. 39 is a schematic side view of an apparatus for correcting spinal deformity in accordance with a sixth embodiment of the present invention.
Figure 41:
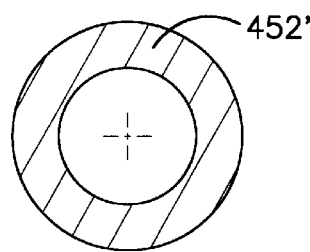
FIG. 41 is a sectional view taken along line 41—41 in FIG. 39.
Figure 40:
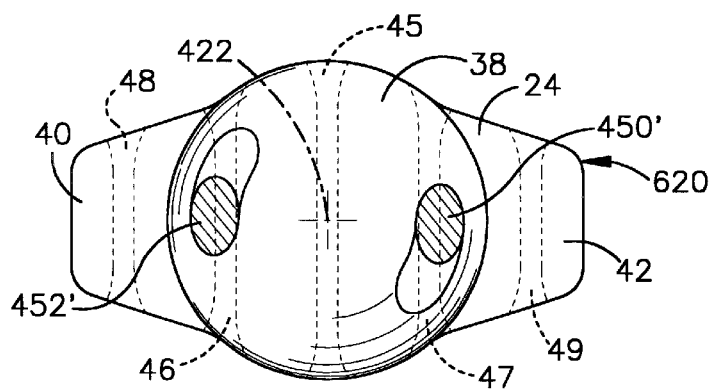
FIG. 40 is a sectional view taken along line 40—40 in FIG. 39.
Figure 42:
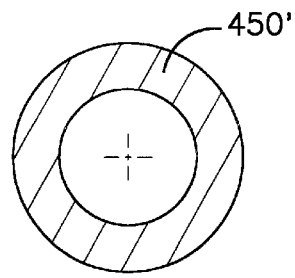
FIG. 42 is a sectional view taken along line 42—42 in FIG. 39.

FIGS. 37 and 38 illustrate an apparatus 510 constructed in accordance with a fifth embodiment of the present invention. In the fifth embodiment of FIGS. 37 and 38, reference numbers that are the same as those used in the fourth embodiment of FIGS. 30–36 designate parts that are the same as parts in the fourth embodiment.

According to the fifth embodiment, the apparatus 510 comprises an anchor 520 having three helical spikes 530, 531, and 532 projecting tangentially from the end surface 38 of the platform 24. The spikes 530–532 extend around the axis 422 and have a conical shape that increases in diameter as the helical spikes extend away from the platform. As shown in FIGS. 37 and 38, each of the helical spikes 530–532 has a solid cross-section. Alternatively, each of the helical spikes 530–532 could have a tubular cross-section.

As shown in FIG. 37, the connecting portions 454 at the proximal ends 460 of the helical spikes 530–532 are spaced 120° apart about the axis 422, which balances the anchor 520 and evenly distributes loads on the helical spikes. The three helical spikes 530–532 extend symmetrically in a conical pattern about the axis 422. It is contemplated, however, that the conical shape of one or more of the helical spikes 530–532 could be different from the other(s) (i.e., one spike being a smaller cone than the others). As shown in FIG. 37, the three helical spikes 530–532 have the same axial length and also have the same cross-sectional shape. It is contemplated, however, that one or more of the helical spikes 530–532 could have different axial lengths. Further, it is contemplated that one or more of the helical spikes 530–532 could have a different cross-sectional shape, such as an oval shape. It also contemplated that the one or more of the helical spikes 530–532 could have different diameters (i.e., one spike being thicker or thinner than the other spike(s)). Finally, it is contemplated that the helical spikes 530–532 should have the same pitch, and that the pitch of the helical spikes would be selected based on the specific surgical application and quality of the bone in which the anchor 520 is to be implanted.

The tip portion 458 of each of the helical spikes 530–532 illustrated in FIG. 37 has an elongated conical shape for penetrating into a vertebrae as the platform 24 of the anchor 520 is rotated in the clockwise direction. It should be understood that the tip portions 458 of the helical spikes 530–532 of the anchor 520 could alternatively be configured like the tip portions illustrated in FIG. 7. Further, although the outer surfaces of the helical spikes 530–532 are shown as being smooth in FIGS. 37 and 38, it is contemplated that the outer surfaces may instead be porous, pitted, or have a biocompatible coating to assist with fixation of the anchor 520 to the vertebrae.

The helical spikes 530–532 of the anchor 520 according to the second embodiment of FIGS. 37 and 38 are also made of a shape memory alloy and are implanted in a vertebrae in the same manner as the anchor 420 according to the fourth embodiment. The shapes of the anchor 520 at various stages of the implantation process are similar to that which is illustrated in FIGS. 34–36 for the anchor 420 of the fourth embodiment. Hence, the shape that is "memorized" into the material of the anchor 520 is illustrated in FIG. 37. Further, the anchor 520 has a first condition (not shown) prior to implantation in a vertebrae in which the helical spikes 530–532 do not have a conical shape, but instead have a generally cylindrical shape with a first maximum diameter. In addition, in the first condition, the helical spikes 530–532 have a first axial length. In order for the anchor 520 to take the shape of the first condition, the temperature of the anchor must be below its TTR so that the material of the anchor is soft and ductile.

To return the helical spikes 530–532 to the conical shape, heat is applied to the anchor 520 until the temperature of the anchor exceeds the TTR for the shape memory material. With the helical spikes 530–532 expanding radially and contracting axially due to the heat, the helical spikes are implanted in a vertebrae in the conical shape, or second condition, as illustrated in FIG. 36 for the fourth embodiment. In the implanted second condition, the helical spikes 530–532 have a second maximum diameter that is larger than the first maximum diameter of the helical spikes in the first condition. Further, in the implanted second condition, the helical spikes 530–532 have a second axial length that is smaller than the first axial length of the helical spikes in the first condition.

It is contemplated that the first and second conditions of the helical spikes 530–532 described above could be achieved even if only certain portions of the helical spikes were made from a shape memory alloy. For example, it is contemplated that the tip portions 458 and the intermediate portions 456 of the helical spikes 530–532 could be made from a shape memory alloy, while the connecting portions 454 are made from another biocompatible metal. Further, if a shape memory material is not used at all in the helical spikes 530–532 and a material such as spring steel is used instead, the helical spikes would still be able to be compressed into the first condition and expand into the second condition upon implantation.

The anchor 520 is implantable into vertebrae in the same manner as the anchor 420 described above. Because the helical spikes 530–532 of the anchor 520 displace less cancellous bone during implantation than a conventional solid shank bone screw, less torque is required to implant the anchor in a vertebrae than is required by a conventional bone screw. Further, the conical shape of the helical spikes 530–532 according to the second embodiment, when implanted in a vertebrae, make the anchor 520 highly resistant to being pulled out of the vertebrae and to toggling in the vertebrae despite being subjected to substantial forces caused by human body movement and muscle memory. As mentioned previously, the conical shape of the helical spikes 530–532 increases the amount of surface area engaged by the anchor 520, distributes any load on the anchor, and provides fixation over a larger volume of bone. Finally, the use of a shape memory alloy for the helical spikes 530–532 allows the anchor 520 to have a smaller diameter prior to implantation, which permits minimally invasive endoscopic surgery through a cannula, and a wider diameter when implanted, which improves fixation in a vertebrae.

Once implanted, the anchor 520 may be used along with the rod 100 and one or more of the cables described above to achieve and maintain correction of spinal deformity.

FIGS. 39–42 illustrate an apparatus 610 constructed in accordance with a sixth embodiment of the present invention. In the sixth embodiment of FIGS. 39–42, reference numbers that are the same as those used in FIGS. 30–36 designate parts that are the same as parts in FIGS. 30–36.

According to the sixth embodiment, the apparatus 610 comprises an anchor 620 having helical spikes 450' and 452'. FIGS. 39–42 illustrate that the connecting portions 454 and the tip portions 458 of the helical spikes 450' and 452' have a solid cross-section, while the intermediate portions 456 have a tubular cross-section. This configuration of the anchor 620 provides means for matching the modulus of elasticity of the bone.

The anchor 620 is implantable into vertebrae in the same manner as the anchor 420 described above. Once implanted, the anchor 620 may be used along with the rod 100 and one or more of the cables described above to achieve and maintain correction of spinal deformity.

FIGS. 43–46 illustrate an apparatus 710 constructed in accordance with a seventh embodiment of the present invention. In the seventh embodiment of FIGS. 43–46, reference numbers that are the same as those used in FIGS. 1–11 designate parts that are the same as parts in FIGS. 1–11.

Figure 46:
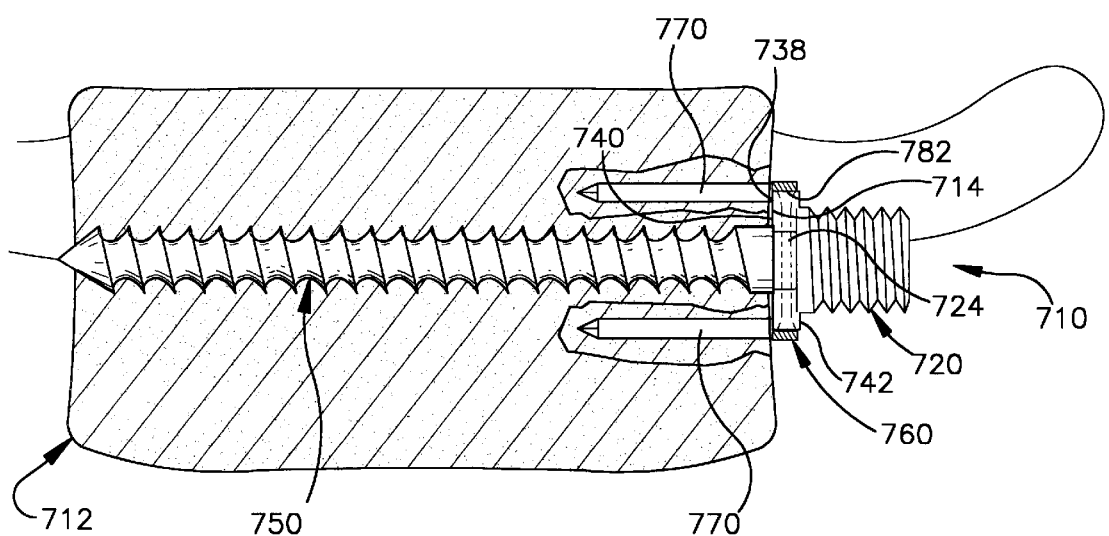
FIG. 46 is a schematic anterior view illustrating the apparatus of FIG. 43 implanted in a vertebrae.

According to the seventh embodiment, the apparatus 710 includes an anchor 720 for implanting in a vertebrae 712 (FIG. 46). The anchor 720 is made from a biocompatible material, such as titanium or stainless steel. It is contemplated that the biocompatible material used for the anchor 720 could also be polymeric or composite (i.e., carbon fiber or other biologic composite) in nature.

The anchor 720 is centered about a longitudinal axis 722 (FIG. 1). The anchor 720 includes a platform 724 having a cylindrical outer surface portion 726 extending between oppositely disposed first and second axial ends 728 and 730 of the platform. The platform 724 includes a generally rectangular slot 732 that extends axially from the first end 728 toward the second end 730 of the platform. Adjacent the first end 728, the outer surface 726 of the platform 724 includes first and second segments of external threads 734 and 736 that are separated by the slot 732. The slot 732 and the threads 734 and 736 provide structure for connecting spinal fixation instrumentation to the platform 724 as discussed further below.

The platform 724 further includes oppositely disposed first and second wing sections 740 and 742 and a plurality of parallel passages 744. The wing sections 740 and 742 extend radially outward from the cylindrical outer surface 726 of the platform 724. As best seen in FIG. 44, each of the passages 744 extends transverse to the axis 722 and is chamfered on both of its ends. In the illustrated embodiment, a centrally located first passage 745 extends through the axis 722. Second and third passages 746 and 747 are located on either side of the centrally located first passage 745. Finally, fourth and fifth passages 748 and 749 are located in the first and second wing sections 740 and 742, respectively. It should be understood that the platform 724 could have more or less than five passages 744.

The second end 730 of the platform 724 includes an end surface 738 that is complimentary to the shape of a side surface 714 (FIG. 46) on the vertebrae 712. It should be understood that the end surface 738 of the platform 724 could be any shape necessary to remain complimentary to the shape of the side surface 714 of the vertebrae 712. The end surface 738 of the platform 724 may include barbs (not shown) or other suitable structure for fixedly engaging the side surface 714 of the vertebrae 712. Further the end surface 738 of the platform 724 may also be porous, pitted, or have a biocompatible surface coating to assist with fixation of the anchor 720 to the vertebrae 712.

A fastener portion 750 of the anchor 720 projects from the second end surface 738. The fastener portion 750 has a solid cross-section, but could alternatively have a hollow or tubular cross-section. It is contemplated that, with a tubular cross-section, the wall thickness can be varied/selected to match the modulus of elasticity of the bone, which can improve fixation strength and load-sharing characteristics of the anchor 720 and the vertebrae 712.

The fastener portion 750 comprises a shaft 752 with an external thread convolution 754 for engaging the vertebrae 712. The thread convolution 754 is a known coarse helical pattern that extends about the axis 722. Although the outer surface of the fastener portion 750 is shown as being smooth, it is contemplated that the outer surfaces may instead be porous, pitted, or have a biocompatible coating to assist with fixation of the anchor 720 to the vertebrae 712.

The fastener portion 750 includes a pointed tip 758. It is further contemplated that the tip portion 758 could be covered with a tip protector (not shown) to prevent accidental sticks to surgical staff and accidental damage to tissue surrounding the vertebrae. Such a tip protector could be made of a bio-absorbable material, such as polylactic acid, or non-bio-absorbable material, such as medical grade silicon. The tip protector would be manually removed or pushed-off during implantation of the anchor 720.

The apparatus 710 includes a staple 760 made of a suitable biocompatible material such as titanium or stainless steel. The staple 760 has a generally rectangular shape with an opening 762 (FIG. 44) for receiving the platform 724 of the anchor 720. A plurality of nail-like projections 770 extend from a lower surface 772 of the staple 760. In the illustrated embodiment, the projections 770 are disposed adjacent the four corners of the staple 760 and are for embedding into the vertebrae 712. A pair of diametrically opposed flanges 780 project from an upper surface (not numbered) of the staple 760. Each of the flanges 780 includes an inwardly facing surface 782 (FIG. 43) for engaging the periphery of the wing sections 740 and 742 of the platform 724.

The apparatus 710 for correcting spinal deformity further includes the rod 100, the lock nut 102, and the cables 120, 150, and 170 described above with regard to the first embodiment. As previously described, one or more of the cables 120, 150, and 170 are used to straighten curvature in the spine prior to attachment of the rod 100 to the anchor 720.

To implant the anchor 720, a pilot hole (not shown) may be drilled in the cortical bone of the vertebrae 712. The tip portion 758 of the fastener portion 750 of the anchor 720 is then placed in the hole in the vertebrae 712 and the rotatable driver 130 (FIG. 45) is inserted into the slot 732 in the platform 724. The driver 130 is then rotated, causing the anchor 720 to rotate as well. Rotation of the anchor 720 screws the fastener portion 750 into the cancellous bone of the vertebrae 712. Continued rotation of the anchor 720 embeds the fastener portion 750 deeper into the cancellous bone of the vertebrae 712. The anchor 720 is rotated until the end surface 738 of the platform 724 seats against the side surface 714 of the vertebrae 712 as shown in FIG. 46.

The staple 760 is then placed over the platform 724 of the anchor 720 and force is applied to the staple to drive the projections 770 into the vertebrae 712. The projections 770 are driven into the vertebrae 712 until the lower surface 772 of the staple 760 contacts the surface 714 of the vertebrae. In this position, as shown in FIG. 46, the inwardly facing surfaces 782 on the flanges 780 of the staple 760 engage the periphery of the wing sections 740 and 742 of the platform 724 to block relative movement between the anchor 720 and the staple. This prevents the anchor 720 from rotating and backing out of the vertebrae 712 and provides stability for the platform 724.

Once two or more of the anchors 720 and associated staples 760 have been implanted in separate vertebrae, one or more of the cables 120, 150, and 170 described above can be used, along with the rod 100 and nuts-102, to achieve and maintain correction of spinal deformity.

From the above description of the invention, those skilled in the art will perceive improvements, changes and modifications. For example, it is contemplated that more than two cables could be used with the apparatuses disclosed above in order to achieve correction in multiple planes. Such improvements, changes and modifications within the skill of the art are intended to be covered by the appended claims.

Having described the invention, I claim:

1. An apparatus for correcting spinal deformity, said apparatus comprising:

at least one anchor for implantation into a vertebral body, said at least one anchor, when implanted, being resistant to toggling in the vertebral body and to being pulled from the vertebral body;

said at least one anchor including a platform having a first surface for facing the vertebral body, said platform including at least one passage extending transversely through said platform, said at least one passage for receiving a cable connected with another vertebral body;

said at least one anchor further including at least one helical spike for embedding into the vertebral body upon rotation of said platform, said at least one helical spike projecting from said first surface on said platform and extending around a longitudinal axis, said at least one helical spike having a tip portion at a distal end which penetrates into the vertebral body as said platform is rotated;

said platform including a plurality of parallel passages extending transversely through said platform and an oppositely disposed pair of radially extending wing sections, one of said plurality of parallel passages extending through each of said pair of wing sections.

2. The apparatus of claim 1 further comprising at one cable extending through one of said plurality of parallel passages in said platform.

3. The apparatus of claim 2 wherein said at least one anchor comprises first and second anchors for implanting in first and second vertebral bodies, respectively, said at least one cable extending through a respective one of said plurality of parallel passages in said platform of each of said first and second anchors, said at least one cable being tensionable to cause relative movement between the first and second vertebral bodies.

4. The apparatus of claim 3 wherein said platform on each of said first and second anchors includes structure for connecting a spinal fixation implant.

5. The apparatus of claim 4 further comprising a spinal fixation implant extending between and connected to said platform on each of said first and second anchors after said at least one cable has been tensioned to effect relative movement between the first and second vertebral bodies.

6. The apparatus of claim 3 wherein said at least one cable includes a primary cable extending between a centrally located one of said plurality of parallel passages in each of said first and second anchors.

7. The apparatus of claim 6 wherein said at least one cable further includes a secondary cable extending between one of said plurality of parallel passages in one of said pair of wing sections on said platform of each of said first and second anchors, said secondary cable being tensionable to cause relative movement between the first and second vertebral bodies in one direction after said primary cable has been tensioned to effect relative movement between the first and second vertebral bodies in another direction.

8. An apparatus for correcting spinal deformity, said apparatus comprising:

first and second anchors for implantation into first and second vertebral bodies, respectively, said anchors, when implanted, being resistant to toggling in the vertebral bodies and to being pulled from the vertebral bodies;

each of said first and second anchors including a platform having at least one passage extending transversely through said platform;

each of said first and second anchors further including screw means for embedding into one of the vertebral bodies upon rotation of said platform, said screw means projecting from said platform on each of said first and second anchors and having a tip portion at a distal end which penetrates into a respective one of the vertebral bodies as said platform is rotated; and at least one cable extending through said at least one passage in said platform on each of said first and second anchors, said at least one cable being tensionable to cause relative movement between the first and second vertebral bodies;

said platform on each of said first and second anchors including a plurality of parallel passages extending transversely through said platform;

said platform on each of said first and second anchors further including an oppositely disposed pair of radially extending wing sections, one of said plurality of parallel passages extending through each of said pair of wing sections on each of said first and second anchors.

9. The apparatus of claim 8 wherein said platform on each of said first and second anchors includes structure for connecting a spinal fixation implant.

10. The apparatus of claim 9 further comprising a spinal fixation implant extending between to said platform on each of said first and second anchors, said spinal fixation implant being fixedly connected to each of said first and second anchors after said at least one cable has been tensioned to effect relative movement between the first and second vertebral bodies.

11. The apparatus of claim 10 wherein said at least one cable includes a primary cable extending between a centrally located one of said plurality of parallel passages in said platform of each of said first and second anchors.

12. The apparatus of claim 11 wherein said at least one cable further includes a secondary cable extending between one of said plurality of parallel passages in one of said pair of wing sections on said platform of each of said first and second anchors, said secondary cable being tensionable to cause relative movement between the first and second vertebral bodies in one direction after said primary cable has been tensioned to effect relative movement between the first and second vertebral bodies in a another direction.

13. An apparatus for correcting spinal deformity, said apparatus comprising:

at least two anchors for implantation into separate vertebral bodies, said at least two anchors, when implanted, being resistant to toggling in the vertebral bodies and to being pulled from the vertebral bodies;

each of said at least two anchors including a platform having at least one passage extending transversely through said platform;

each of said at least two anchors further including at least two helical spikes for embedding into one of the vertebral bodies upon rotation of said platform, said at least two helical spikes projecting from said platform on each of said at least two anchors and having tip portions at a distal end which penetrate into a respective one of the vertebral bodies as said platform is rotated;

at least one cable extending through said at least one passage in said platform on each of said at least two anchors, said at least one cable being tensionable to cause relative movement between the vertebral bodies; and a spinal fixation implant extending between and is connectable with said platform on each of said at least two anchors.

14. The apparatus of claim 13 wherein said platform on each of said at least two anchors includes a plurality of parallel passages extending transversely through said platform.

15. The apparatus of claim 14 wherein said platform on each of said at least two anchors includes an oppositely disposed pair of radially extending wing sections, one of said plurality of parallel passages extending through each of said pair of wing sections on each of said at least two anchors.

16. The apparatus of claim 15 wherein said at least one cable includes a primary cable extending between a centrally located one of said plurality of parallel passages in said platform of each of said at least two anchors.

17. The apparatus of claim 16 wherein said at least one cable further includes a secondary cable extending between one of said plurality of parallel passages in one of said pair of wing sections on said platform of each of said at least two anchors, said secondary cable being tensionable to cause relative movement between the vertebral bodies in one direction after said primary cable has been tensioned to effect relative movement between the vertebral bodies in a another direction.

18. The apparatus of claim 13 wherein each of said at least two anchors has three helical spikes.

19. The apparatus of claim 13 wherein said at least two helical spikes on each of said at least two anchors, when implanted, have a conical shape that increases in diameter as said at least two helical spikes extend away from said platform on each of said at least two anchors.

20. A method for correcting spinal deformity, said method comprising the steps of:

providing at least two anchors for implantation into separate vertebral bodies, each of the at least two anchors including a platform having at least one passage extending transversely through the platform, each of the at least two anchors further including screw means for embedding into one of the vertebral bodies upon rotation of the platform;

implanting the at least two anchors in the separate vertebral bodies;

connecting the at least two anchors with at least one cable that extends through the at least one passage in the platform on each of the at least two anchors;

tensioning the at least one cable to cause relative movement between the vertebral bodies; and connecting a spinal fixation implant to the platform on each of the at least two anchors.

21. A method for correcting spinal deformity, said method comprising the steps of:

providing at least two anchors for implantation into separate vertebral bodies, each of the at least two anchors including a platform having at least one passage extending transversely through the platform, each of the at least two anchors further including screw means for embedding into one of the vertebral bodies upon rotation of the platform;

implanting the at least two anchors in the separate vertebral bodies;

connecting the at least two anchors with at least one cable that extends through the at least one passage in the platform on each of the at least two anchors; and tensioning the at least one cable to cause relative movement between the vertebral bodies;

the platform on each of the at least two anchors including a plurality of parallel passages extending transversely through the platform, the platform on each of the at least two anchors further including an oppositely disposed pair of radially extending wing sections, one of the plurality of parallel passages extending through each of the pair of wing sections on each of the at least two anchors.

22. The method of claim 21 further comprising the steps of:

extending a primary cable between a centrally located one of the plurality of parallel passages in the platform of each of the at least two anchors; and tensioning the primary cable to cause relative movement between the vertebral bodies in one direction.

23. The method of claim 22 further comprising the steps of:

extending a secondary cable between one of the plurality of parallel passages in one of the pair of wing sections on the platform of each of the anchors; and tensioning the secondary cable to cause relative movement between the vertebral bodies in another direction.

24. The method of claim 23 further comprising the step of:

connecting a spinal fixation implant to the platform on each o the at least two anchors.

25. An apparatus for correcting spinal deformity, said apparatus comprising:

at least one anchor for implantation into a vertebral body, said at least one anchor having a longitudinal axis and, when implanted, being resistant to toggling in the vertebral body and to being pulled from the vertebral body;

said at least one anchor including a platform having a first surface for facing the vertebral body, said first surface being solid and extending generally transverse to said longitudinal axis, said platform including at least one passage extending transversely through said platform, said at least one passage for receiving a cable connected with another vertebral body;

said at least one anchor further including at least one helical spike for embedding into the vertebral body upon rotation of said platform, said at least one helical spike projecting tangentially from said first surface on said platform and extending around said longitudinal axis, said at least one helical spike having a tip portion at a distal end which penetrates into the vertebral body as said platform is rotated.

26. The apparatus of claim 25 wherein said platform includes a plurality of parallel passages extending transversely through said platform.

27. The apparatus of claim 25 wherein said at least one anchor has a pair of helical spikes extending around said longitudinal axis, said proximal ends of said pair of helical spikes being spaced 180° apart.

28. The apparatus of claim 25 wherein said at least one anchor has three helical spikes extending around said longitudinal axis, said proximal ends of said helical spikes being spaced 120° apart.

29. The apparatus of claim 25 wherein said first surface on said platform of said at least one anchor has a shape that is complimentary to the shape of an outer surface of the vertebral body for engaging the outer surface of the vertebral body.

30. The apparatus of claim 25 wherein said at least one helical spike, when implanted, has a conical shape that increases in diameter as said at least one helical spike extends away from said platform.

31. The apparatus of claim 25 wherein at least a portion of said at least one helical spike is made of a shape memory alloy that is responsive to changes in temperature above and below a predetermined temperature transition range, said at least one helical spike being in said first condition when the temperature of said at least one helical spike is below said predetermined temperature transition range, said at least one helical spike being in said second condition when heated above said predetermined temperature transition range, said at least one helical spike being implanted into the vertebral body in said second condition.

32. The apparatus of claim 31 wherein said at least one helical spike further has a connecting portion at a proximal end connected to said platform and an intermediate portion extending between said connecting portion and said tip portion, at least one of said intermediate portion and said tip portion being made of said shape memory alloy.

33. The apparatus of claim 25 wherein said at least one helical spike has a solid cross-section.

34. The apparatus of claim 25 wherein said at least one helical spike has a tubular cross-section.

35. The apparatus of claim 25 wherein a first portion of said at least one helical spike has a solid cross-section and a second portion of said at least one helical spike has a tubular cross-section.

36. An apparatus for correcting spinal deformity, said apparatus comprising:

first and second anchors for implantation into first and second vertebral bodies, respectively, said anchors, when implanted, being resistant to toggling in the vertebral bodies and to being pulled from the vertebral bodies;

each of said first and second anchors having a longitudinal axis and including a platform having at least one passage extending transversely through said platform, each of said platforms having a first surface that is solid and that extends generally transverse to said longitudinal axis;

each of said first and second anchors further including at least two helical spikes for embedding into one of the vertebral bodies upon rotation of said platform, said at least two helical spikes projecting tangentially from said first surface platform on each of said first and second anchors and having a tip portion at a distal end which penetrates into a respective one of the vertebral bodies as said platform is rotated; and at least one cable extending through said at least one passage in said platform on each of said first and second anchors, said at least one cable being tensionable to cause relative movement between the first and second vertebral bodies.

37. The apparatus of claim 36 wherein said platform on each of said first and second anchors includes a plurality of parallel passages extending transversely through said platform.

38. The apparatus of claim 36 wherein said at least two helical spikes on each of said first and second anchors, when implanted, have a conical shape that increases in diameter as said at least two helical spikes extend away from said platform on each of said first and second anchors.

* * * * *